(12) United States Patent
Omary et al.

(10) Patent No.: US 10,253,255 B2
(45) Date of Patent: Apr. 9, 2019

(54) PHOSPHORESCENT NANOPARTICLES AND THEIR USES IN BIOSENSING AND BIOIMAGING

(71) Applicant: University of North Texas, Denton, TX (US)

(72) Inventors: Mohammad A. Omary, Denton, TX (US); Sreekar Marpu, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 4 days.

(21) Appl. No.: 15/365,031

(22) Filed: Nov. 30, 2016

(65) Prior Publication Data
US 2017/0151350 A1   Jun. 1, 2017

Related U.S. Application Data

(60) Provisional application No. 62/261,172, filed on Nov. 30, 2015.

(51) Int. Cl.
| | |
|---|---|
| *C09K 11/70* | (2006.01) |
| *C09K 11/08* | (2006.01) |
| *C09K 11/02* | (2006.01) |
| *C09K 11/87* | (2006.01) |
| *C09K 11/06* | (2006.01) |
| *B82Y 40/00* | (2011.01) |
| *B82Y 20/00* | (2011.01) |
| *B82Y 5/00* | (2011.01) |
| *B82Y 15/00* | (2011.01) |
| *B82Y 30/00* | (2011.01) |

(52) U.S. Cl.
CPC ........ *C09K 11/0883* (2013.01); *C09K 11/025* (2013.01); *C09K 11/06* (2013.01); *C09K 11/70* (2013.01); *C09K 11/87* (2013.01); *B82Y 5/00* (2013.01); *B82Y 15/00* (2013.01); *B82Y 20/00* (2013.01); *B82Y 30/00* (2013.01); *B82Y 40/00* (2013.01); *C08J 2305/08* (2013.01); *C09K 2211/188* (2013.01); *Y10S 977/774* (2013.01); *Y10S 977/896* (2013.01); *Y10S 977/92* (2013.01)

(58) Field of Classification Search
CPC .... A61K 49/0015; C09K 11/00; C09K 11/70; C09K 11/71; C09K 11/717; C09K 11/73
See application file for complete search history.

(56) References Cited

U.S. PATENT DOCUMENTS

2012/0065614 A1*   3/2012   Omary ............... A61K 41/0052
                                                                  604/500

* cited by examiner

*Primary Examiner* — Micah Paul Young
(74) *Attorney, Agent, or Firm* — Jackson Walker LLP

(57) ABSTRACT

Size-tunable phosphorescent particles may be formed through self-assembly of biocompatible linear polymers, such as chitosan and other linear polymers, that bear positive surface charges, through polyelectrolytic complexation to a polyanionic metal phosphor, such as polyanionic gold(I) phosphor (AuP). The phosphorescent hydrogel nanoparticles and thin films thereof are useful for imaging, sensing of biological molecules, detection of hypoxia, and light-emitting devices. The phosphorescent hydrogel particles can be formed from a variety of linear polymers by physical cross-linking using polyelectrolytic light-emitting species, without the need for the phosphorescent complex to be entrapped in an existing microsphere or nanosphere polymer particle.

6 Claims, 21 Drawing Sheets

Biologically-benign polymer: Chitosan

Stimuli-sensitive biocompatible polymers:
Polyethyleneimine   Poly-N-isopropylacryl amide Industrial Polymers:
Polydiallyl dimethyl ammonium chloride   Polyacrylo Nitrile PAA (Poly acrylic acid)   Alginic acid

*Over-expressed molecule in cancers:* Sialyl Lewis x

*Amino acids:*

Arginine    Lysine

*Proteins and other biopolymers:*

Protamine, Lysozyme

Bovine serum albumin (BSA)

A

B

PHOSPHORESCENT NANOPARTICLES AND THEIR USES IN BIOSENSING AND BIOIMAGING

This application claims priority to U.S. Provisional Patent Application Ser. No. 62/261,172, entitled "Phosphorescent Nanoparticles and Their Uses in Biosensing and Bioimaging," filed on Nov. 30, 2015, the entire contents of which are hereby incorporated by reference.

The present invention used in part funds from the National Science Foundation (NSF), Grant Nos. CHE-1413641, CHE-0911690, CMMI-0963509, CHE-0840518, and CHE-1004878, and the Robert A. Welch Foundation, Grant No. B-1542. The United States Government has certain rights in the invention.

BACKGROUND

This disclosure pertains to light-emitting nanoparticles and their uses in biological imaging and sensing applications.

Development of light-emitting polymer nano/micro particles is usually hampered by inherent drawbacks such as photobleaching, stability, and functionalization issues resulting from fluorescent/dye dopants. Formation of biocompatible, luminescent polymer particles often entails hazardous chemical cross-linking processes and/or doping with fluorophores susceptible to leaching and photobleaching.

Growing research interests over the usage of luminescent nanomaterials for diverse biomedical and materials applications have led to the development of various approaches to overcome underlying drawbacks. Numerous efforts are ongoing to address limitations in brightness, biocompatibility, bioconjugation, functionalization, solubility, and/or stability so as to bring the light-emitting material closer to practicality for each particular application. Doping and chemically-conjugating a light-emitter to a host matrix (e.g., polymer, silica/aluminosilica sol-gel matrix, or a carbon nanotube) represent two popular approaches that have met excellent success for enhancing the solubility and stability of luminescent systems. Nevertheless, issues related to guest leakage, complexities in nanoparticle formulations, and/or toxicity of cross-linkers necessitate further research for developing alternative materials and more facile techniques. Polyelectrolytic self-assembly techniques are advantageous in terms of simplicity for synthesizing a variety of nanostructures.

Fluorescent polyelectrolyte structures are considered advantageous compared to dye doped particles for minimizing diffusion or dissolution of dye. However, common fluorescent polyelectrolytic systems employed continue to suffer poor selectivity, photostability, and low quantum efficiency. Fluorescent systems based on pure organic moieties are liable to quenching when interfaced with polymer or host matrices compared to organometallic systems. Phosphorescent systems offer numerous advantages over fluorescent analogues, such as higher efficiencies in electroluminescence (devices based on phosphorescence can exhibit 4× higher efficiency compared to fluorescent ones possessing the same photoluminescence quantum yield), hypoxia sensing, amelioration of background interference (e.g., autofluorescence by endogenous biomolecules and host matrices) by time-based analysis, all of which can be major obstacles in different applications with fluorescence-based systems.

Well-known phosphorescent molecular systems based on Ru(II) or Ir(III) have been utilized in material design through doping techniques; however, the rational engineering of luminescent nanoparticles remains an elusive goal. There has been significant interest in utilizing benign linear polymers such as chitosan in the synthesis of advanced functional materials for biomedical applications because of its well-established biocompatibility and aqueous solubility. Water-soluble polymer systems are also advantageous for materials applications, such as solution processing of multi-layered polymer light-emitting diodes (PLEDs) and electronically-active conductive hydrogels. In fact, the use of both water- and organic-processed layers has proved to be an excellent method for depositing different electronic layers with minimal interference of the others. Whereas all-organic-media-processed devices can lead to interlayer mixing, degradation, and/or other parasitic effects—due to the layers having similar solubilites in the same organic or aqueous phase—alternating water-processed and organic-processed layers helps minimize these issues due to the inherent lower material solubility among successively-deposited layers. For instance, one could deposit a hole-injecting layer (HIL) from an aqueous phase, followed by a hole-transporting (HTL) and/or electron-blocking (EBL) layer from organic media, such as toluene or chlorobenzene, then a light-emitting layer (EML) of the type described in this work from aqueous solution, and finally an electron-transporting layer (ETL) from organic media—if needed (given the dual EML/ETL function of some compositions herein that may preclude the need for a separate ETL). The incompatible solubility between adjacent layer materials in organic vs. aqueous media or phases minimizes invasive interactions between the two deposited layers, hence warranting exciton and/or polaron confinement in the designated layer function(s).

Among existing techniques for synthesizing microparticles and nanoparticles from chitosan polysaccharides and other linear polymers, polyelectrolyte complexation or ionic gelation processes are highly preferred for their simplicity and because they do not rely on toxic chemical cross-linkers. Categorically, past efforts at incorporating luminescent moieties into chitosan nanomaterials have focused on doping or chemically-cross-linking fluorophores including organic dyes, such as fluorescein isothiocyanate (FITC), semiconductor quantum dots, or phosphorescent lanthanide chelates. In all these cases, however, chitosan was used as a capping agent or surfactant to overcome the toxicity or insolubility of luminophores and their incorporation required multiple steps. For example, studies detailing the synthesis of fluorescent chitosan nanoparticles using FITC-labeled chitosan employed a multistep microemulsion technique that included the non-luminescent cross-linkers 1-ethyl-3-(3-dimethylaminopropyl)carbodiimide hydrochloride (ED-C.HCl) and tartaric acid.

Though chemical crosslinking will allow for the formation of micro/nanoparticles, during this process of chemical crosslinking the inherent properties of polymers are sacrificed due to the presence of additional chemical entities. Introducing additional cross-linkers or additives are also known to compromise the optical properties of fluorescent systems, resulting in sub-standard formulations. These drawbacks arise from chemical bonding between the host matrices and the fluorescent dyes that could be easily avoided by polyelectrolyte complexation, which completely relies on electrostatic interactions between oppositely-charged luminescent moieties and host matrix materials. The strength of ionic or physical cross-linking interactions can be easily tuned by variations in pH or ionic strength of the medium in order to favor weaker or stronger interactions that would then allow for size tunability of the polymer particles.

SUMMARY

The present disclosure relates generally to phosphorescent nanoparticles useful for imaging, sensing and detection. In particular, described herein is a novel method for making phosphorescent hydrogel particles from a variety of linear polymers by physical cross-linking using polyelectrolytic light-emitting species.

Methods described herein include the formation of size-tunable phosphorescent particles via self-assembly of biocompatible linear polymers, such as chitosan and other linear polymers, that bear positive surface charges and can be complexed to a polyanionic metal phosphor, such as polyanionic gold(I) phosphor (AuP). The in situ self-assembly of phosphorescent nanoparticles is enabled by the metal phosphor (such as AuP) that performs a quadruple role: a physical cross-linker, light emitter, sensor of polysaccharide rings with structures akin to those of some cancer markers, and contrast agent for electron microscopy. Size tunability in phosphorescent particles is achieved by systematic variations in pH or reactant concentrations. AuP, for example, exhibits "on-off" photoluminescence (PL) switching induced by several amine-bearing linear polymers, rendering the phosphorescent nanocomposites particularly attractive for biological imaging and sensing applications. Finally, in a preferred embodiment, combination of AuP-chitosan with a Pt-based orange-red phosphor leads to white-emitting thin films with high color-rendering index (CRI), remarkable stability, and PL quantum yields as high as 78% with <2% photobleaching. These properties render such thin films useful for applications in lighting and electronic displays.

New embodiments and methods are also described herein for the detection of trace amounts (part-per-million, ppm, levels) of cancer marker-like molecules or polymers, as well as other biological abnormalities and markers thereof, using the phosphorescent nanoparticles disclosed herein. The materials exhibit vanishing poor fluorescence or phosphorescence in water alone but adding ppm levels of cancer markers like molecules or polymers turns on the light emission rather easily and efficiently via a simple, one-step detection method. These biocompatible linear polymers can form nanoparticles with greatly-sensitized phosphorescence in an aqueous environment without the need for doping a phosphorescent complex into an existing polymer microsphere or nanosphere particles.

The compositions described herein for detection of cancer markers and/or similar polymers or biomolecules are highly differentiated. Other alternative luminescent molecular systems that can perform or exhibit similar detection capabilities are highly unlikely, and design alterations are not guaranteed to deliver the same functions. While some molecular systems already in existence can exhibit similar variations in brightness due to variations in percentage of oxygen, pH, or temperature, and some colloidal/molecular systems are known to exhibit enhanced brightness when entrapped into particles or similar matrices, these known compositions cannot be compared for variations in brightness and do not exhibit the on/off signal switching capability exhibited by the composition proposed in this invention in presence of cancer markers and analogous polysaccharides. Some of these known compositions that exhibit enhanced brightness in the presence of colloidal matrices or in the presence of other stimuli involve laborious synthetic process, undesired crosslinking chemistry, and are highly subjected to photo-bleaching. All these additional steps and disadvantages have been completely overcome in the present compositions.

Furthermore, tumor-associated glycans including Sialyl Lewis structures and special antigens are generally screened and identified by introducing a carbohydrate/oligosaccharide-recognizing domain to a modified protein, which is a skill-specific and laborious process. By contrast, the compositions described herein allow for simple and straightforward diagnosis of such tumor-associated biomolecules.

DETAILED DESCRIPTION OF PREFERRED EMBODIMENTS

Figure 1:
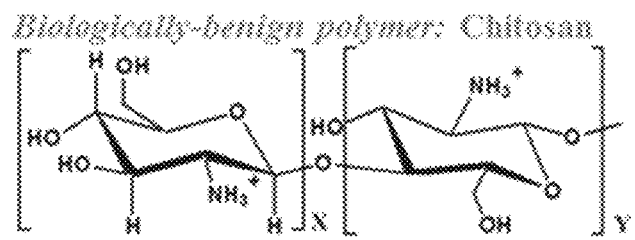
FIG. 1 shows chemical structures of examples of various polymers useful in the present compositions.
Figure 1:
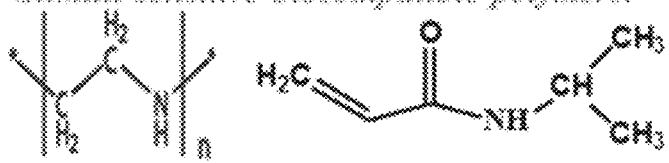
Figure 1:
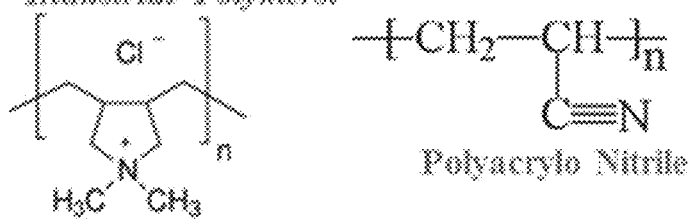
Figure 1:
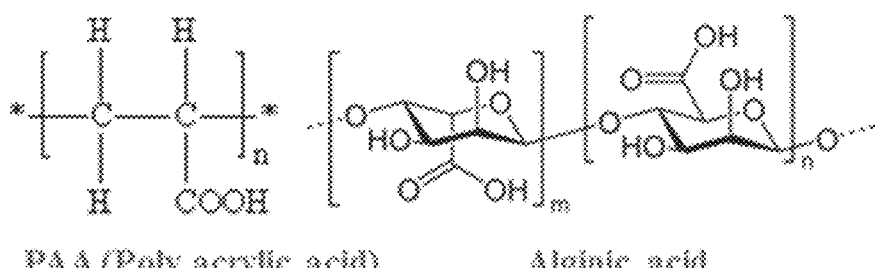

Generally, the present disclosure relates to phosphorescent nanoparticles useful in sensing, imaging and detecting applications.

In summary, a simple polyelectrolyte self-assembly approach can be effectively employed to synthesize stable, size-tunable phosphorescent hydrogel nanoparticles ("PHNPs") in a single step using a phosphorescent complex that, in an unprecedented manner, simultaneously acts as a physical cross-linker and light emitter. The size and stability of PHNPs is controlled by balancing electrostatic interactions between the polymer, such as chitosan, and the phosphor moieties, such as AuP, through variation of simple experimental parameters, including host/guest concentration, pH, and ionic strength. Owing to retained guest emission, consistent PL enhancement, microsecond lifetimes and sensitivity to micromolar concentration of positively charged polymers, the ability of AuP to act not only as a physical cross-linker but also as a promising sensing agent makes it particularly useful in preferred embodiments. The present compositions and methods use metal phosphors such as AuP and analogues thereof as phosphorescent physical cross-linkers for a broad domain of positively-charged amine-based polymers and biomolecules. Additional applications in photonic sensors and molecular electronic devices are also demonstrated based on this strategy, for example toward multi-layer deposition of solution-processed organic light-emitting diodes.

In embodiments of the present disclosure, a gold phosphor "AuP"=$[Au^I(TPPTS)_3]^{8-}$ (TPPTS=tris(3,3',3"-trisulfonatophenyl)phosphine) and a platinum phosphor "PtP"=$Pt^{II}(ptp)_2$ (ptp=3,5-bis(pyridyl)-1,2,4-triazolate) are used as light emitters and physical cross-linkers, simultaneously. The gold phosphors denoted "AuP" may also be defined as =$M_8[Au(TPPTS)_3]$, where TPPTS=tris(3,3',3"-trisulfonatophenyl)phosphine) and M=Na, K, Cs, or similar metal. Another platinum phosphor defined as $M_4[Pt_2(P_2O_5H_2)_4]\cdot 2H_2O$=metal dihydrotetrakis(pyrophosphito) platinum(II), a.k.a. "Pt—POP", where the M metal is potassium (K) or sodium (Na), is also used as a light emitter in phosphorescent nanoparticle compositions or biological environments to monitor and sense hypoxia.

While similar molecular complexes are known to possess biological activity, there have been no reports of encapsulation of such species into nanoparticles. This is significant because of the known advantages of utilizing nanoparticles for applications in targeted drug delivery and bioimaging. Chitosan polysaccharides, in particular, are also remarkably similar in structure to the important blood group antigen, Sialyl Lewis X, a tetrasaccharide that plays a vital role in cell-to-cell recognition and is secreted in hypoxia-stimulated colon and breast cancers, among other metastatic cancer cells. Therefore, phosphorescent chitosan hydrogel nanoparticles ("PCHNPs") have the potential for a multitude of biomedical applications including imaging, sensing, and detection. Cytotoxicity assays of PCHNPs in SNU-5 cell lines demonstrate no cytotoxicity at concentrations relevant for such biomedical applications, confirming their benign composition. Furthermore, the realization of white-phosphorescent thin films from aqueous polymer blends with remarkable photostability and brightness could prove to be highly useful. A variety of biocompatible linear polymers—including chitosan, poly-L-lysine (PLL), poly-ethyleneimine (PEI), poly-diallyldimethylammonium chloride (PDADMAC), polyacrylo nitrile (PAN), and polyacrylic acid (PAA)—can be processed into phosphorescent nanoparticles without the need for the phosphorescent complex to be doped in an existing microsphere or nanosphere polymer particle.

Figure 2:
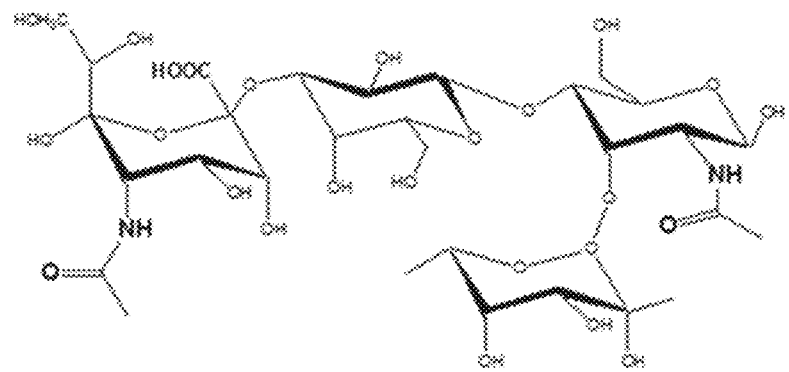
FIG. 2 shows chemical structures of examples of various biological molecules which may be targeted or sensed using the present compositions.
Figure 2:
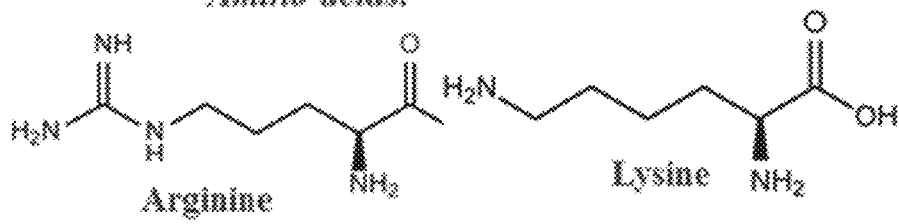
Figure 2:
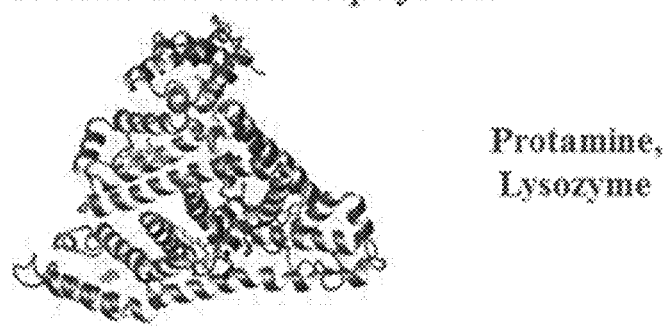

FIG. 1 shows the chemical structures of representatives of various exemplary polymers that are useful in the present nanoparticles and methods. FIG. 2 shows the chemical structures of various exemplary biological markers, including cancer marker molecules, which can be targeted using the present nanoparticles and methods. Chitosan polysaccharides and their parent chitin form, in particular, are remarkably similar in structure to the important blood group antigen, Sialyl Lewis X, a tetrasaccharide that plays a vital role in cell-to-cell recognition and is secreted in hypoxia-stimulated colon and breast cancers, among other metastatic cancer cells. Hence, sensing and detection of chitosan and other amine-bearing polymers at ppm levels provides a platform for sensing cancer markers and other biological molecules that exhibit similar chemical structures and functional groups to those in the polymers sensed. Therefore, the phosphorescent molecules and polymer hydrogel nanoparticles described herein have the potential for a multitude of biomedical applications including imaging, sensing, and detection.

Preferred embodiments pertain to phosphorescent hydrogel nanoparticles comprising: polyanionic metal phosphors having light emitting properties and biocompatible linear polymers that are cross-linked and complexed through electrostatic interactions with the polyanionic metal phosphors. The polyanionic metal phosphors emit light when complexed with the biocompatible linear polymers. In additional preferred embodiments, the polyanionic metal phosphors are "AuP," "PtP," "Pt—POP," or a combination thereof. In additional preferred embodiments, the polyanionic metal phosphors are "AuP," wherein "AuP" is $M_8[Au(TPPTS)_3]$, and wherein TPPTS is tris(3,3',3"-trisulfonatophenyl)phosphine) and M is potassium, sodium, cesium, or a similar metal. In additional preferred embodiments, the polyanionic metal phosphors are "PtP," wherein "PtP" is $Pt^{II}(ptp)_2$, and wherein ptp is 3,5-bis(pyridyl)-1,2,4-triazolate). In additional preferred embodiments, the polyanionic metal phosphors are "Pt—POP," wherein "Pt—POP" is $M_4[Pt_2(P_2O_5H_2)_4]\cdot 2H_2O$, and wherein $P_2O_5H_2$ is dihydrotetrakis(pyrophosphite) and M is potassium or sodium. In additional preferred embodiments, the biocompatible linear polymers are chitosan polymers, poly-L-lysine (PLL), poly-ethyleneimine (PEI), poly-diallyldimethylammonium chloride (PDADMAC), polyacrylo nitrile (PAN), polyacrylic acid (PAA), or a combination thereof.

Preferred embodiments also pertain to phosphorescent thin films, which may be processed from aqueous solutions, comprising: polyanionic metal phosphors having light emitting properties and biocompatible linear polymers that are complexed through electrostatic interactions with the polyanionic metal phosphors. In additional preferred embodiments, the polyanionic metal phosphors are "AuP," "PtP," "Pt—POP," or a combination thereof. In additional preferred embodiments, the polyanionic metal phosphors are "AuP," wherein "AuP" is $M_8[Au(TPPTS)_3]$, and wherein TPPTS is tris(3,3',3"-trisulfonatophenyl)phosphine) and M is potassium, sodium, cesium, or a similar metal. In additional preferred embodiments, the polyanionic metal phosphors are "PtP," wherein "PtP" is $Pt^{II}(ptp)_2$, and wherein ptp is 3,5-bis(pyridyl)-1,2,4-triazolate). In additional preferred embodiments, the polyanionic metal phosphors are "Pt—POP," wherein "Pt—POP" is $M_4[Pt_2(P_2O_5H_2)_4].2H_2O$, and wherein $P_2O_5H_2$ is dihydrotetrakis(pyrophosphite) and M is potassium or sodium. In additional preferred embodiments, the biocompatible linear polymers are chitosan polymers, poly-L-lysine (PLL), poly-ethyleneimine (PEI), poly-diallyldimethylammonium chloride (PDADMAC), polyacrylo nitrile (PAN), polyacrylic acid (PAA), or a combination thereof.

Additional preferred embodiments pertain to the use of the phosphorescent thin films in a light-emitting device, where the light-emitting device may be a light-emitting diode (LED), a fluorescent lamp, or an organic light-emitting diode (OLED). Additional preferred embodiments pertain to the use of the phosphorescent thin films as sensors.

In preferred embodiments, the phosphorescent molecules are useful for sensing the presence of a biomolecule that can exhibit a positive charge in a sample. In this method, the sample is contacted with a polyanionic metal phosphor, which can be "AuP", "PtP", or "Pt—POP", or a combination thereof, to produce a mixed sample, then light emission is detected from the mixed sample, wherein the presence of light emission indicates the presence of the biomolecule. In additional preferred embodiments, the biomolecule to be sensed is a polypeptide or a polysaccharide. In additional preferred embodiments, the biomolecule is a polypeptide that is poly-L-lysine or a polysaccharide that is the cancer marker Sialyl Lewis X.

Additional preferred embodiments pertain to a method for sensing the presence of hypoxia in a sample taken from a biological environment. First, the sample is contacted with a polyanionic metal phosphor having light emitting properties to produce a mixed sample, wherein the polyanionic metal phosphor is "Pt—POP," wherein "Pt—POP" is $M_4[Pt_2(P_2O_5H_2)_4].2H_2O$, and wherein $P_2O_5H_2$ is dihydrotetrakis(pyrophosphite) and M is potassium or sodium. Next, light emission is detected from the mixed sample, wherein the presence of light emission indicates the presence of hypoxia in the biological environment.

Example 1. Methods and Materials

Medium molecular weight chitosan (85% deacetylated) and other chemicals required for the syntheses of AuP were purchased from Sigma-Aldrich (St. Louis, Mo.) and Strem Chemicals (Newburyport, Mass.) while 18.2 MQ-cm millipore water was used for all synthetic transformations. Chitosan polymer solutions were first homogenized, and phosphorescent chitosan hydrogel nanoparticles (PCHNPs) were synthesized by simple dropwise addition of the required concentrations of AuP (see Example 2 for synthesis details) into the chitosan polymer solutions maintained at a specific pH, which was adjusted using acetic acid or ammonium hydroxide. These PCHNP aqueous dispersions were either freeze-dried or dried under ambient conditions to form xerogel films directly on glass slides. Synthetic details on the preparation of xerogels include simple freeze drying of hydrogel materials in solution at liquid nitrogen temperature and under vacuum for 2 to 3 hours, until a fibrous and porous xerogel material is formed.

An intermediate hydrogel aggregate form was prepared in the same manner by which the aforementioned PCHNP aqueous dispersions were prepared but under the particular variation whereby the mixing quantities are adjusted to 0.25% chitosan and >0.5 M AuP. Meanwhile, all polymers, monomers and biomolecules listed herein in addition to chitosan, i.e., poly-L-lysine (PLL), poly-ethyleneimine (PEI), poly-diallyldimethylammonium chloride (PDADMAC), polyacrylo nitrile (PAN), polyacrylic acid (PAA), alginic acid, sialyl lewis X, lysine, arginine, and bovine serum albumin were all directly purchased from Sigma-Aldrich and used without further purification. Sensing of these polymers or chitosan was attained simply by adding small amounts (ppm levels) by a micropipette to an aqueous solution of dilute AuP (1 μM-1 mM concentration) to turn on its emission.

For TEM and SEM analysis, a few drops of as-prepared PCHNP sample solution was drop-casted on the respective grids. PCHNP films were made by simple evaporation of solution on a clean glass slide. Both AuP and PtP were separately dissolved/dispersed in chitosan solution followed by mixing of two solutions in different weight percent ratios result in formation of AuP—PtP hybrid systems.

Photoluminescence Characterization:

Steady-state photoluminescence spectra were acquired with a PTI Quanta-Master model QM-4 (Photon Technology International, Edison, N.J.) scanning spectrofluorometer. The relative quantum yield (RQY) measurements were performed by comparing with standard quinine sulfate. The relative quantum yield was calculated from ratio of absorption intensity and photoluminescence intensity data generated for both standard and samples of interest using the equation $Q_{(sm)}=Q_{(st)}*\{Abs_{(st)}/Abs_{(sm)}\}*\{Emi_{(sm)}/Emi_{(st)}\}*\{RI_{(sm)}/RI_{(st)}\}$ where sm indicates sample of interest and st indicates standard, while Q=Quantum yield, Abs=Absorbance Intensity, Emi=Emission Intensity, RI=Refractive index of the medium. Before examining RQY of PCHNP colloidal system, the RQY of universal standard fluorophore quinine sulfate was examined for both reproducibility and for establishing experimental protocol. Quantum yield of quinine sulfate solution was used as reference for calculating RQY of PCHNPs colloidal system. The obtained values for quinine sulfate were in good agreement with literature. The lifetime values were acquired with a xenon arc flash lamp and a pulsed nitrogen laser interfaced with a tunable dye laser and a frequency doubler, as part fluorescence and phosphorescent sub-system add-ons to the PTI instrument.

Cell Viability.

SNU-5 cells were purchased from ATCC (cat. # CRL-5973) (American Type Culture Collection, Manassas, Va.), and maintained in Iscove's Modified Dulbecco's Medium (IMDM) (ATCC, cat. #30-2005) with 10% FBS (Fisherbrand Research Grade Fetal Bovine Serum, cat. #03-600-511) (Fisher Scientific UK Ltd., Loughborough). Cells (10,000/well) were seeded on 96-well plates and the desired particle amounts were added to the wells. The plates were incubated for an additional 24 h at 37° C. (5% $CO_2$). After incubation, cell viability was evaluated using MTT. MTT dissolved in culture media (5 mg/mL) was added to each well (25 L/well). The cells were incubated for 4 h at 37° C. (5% $CO_2$) after which time 0.08 M HCl in 2-propanol (100 L/well) was added. Light absorption was measured on a Synergy 2 multi-mode microplate reader (BioTek, Winooski, Vt.). The viability of the cells exposed to particles was expressed as a percentage of the viability of cells grown in the absence of particles on the same plate.

Example 2. Mechanism of Formation and Synthesis

Mechanism of Formation and Synthesis of PCHNPs by Polyanionic Self-Assembly Approach.

AuP and PtP were synthesized and characterized according to literature procedures, or slight modifications of literature procedures. AuP is synthesized by simple mixing and stirring of TPPTS ((3,3',3"-Phosphanetriyltris(benzenesulfonic acid) trisodium salt) ligand obtained directly from Sigma-Aldrich with Au(THT)Cl (gold(I) thetrahydrothiophene chloride). Three to one molar equivalents of TPPTS ligand and Au(THT)Cl were mixed in the water: dichloromethane mixture, the solution was stirred at room temperature for two to three hours and later the solid was extracted by simple freeze-dry vacuum technique. The extracted solid was characterized by various spectroscopy techniques.

Pt—POP was synthesized by a novel microwave-assisted synthetic method. For the latter novel method, to synthesize the $K_4[Pt_2(P_2O_5H_2)]\cdot 2H_2O$ embodiment, for example, 0.4 grams of $K_2PtCl_4$ and 1.5 grams of $H_3PO_3$ were combined into a 10 mL microwave reactor flask. Approximately 5 mL of Millipore water was added, and the flask containing the dark red slurry was sealed. The reaction was completed in 30 minutes at 90° C. using a CEM Discover S-Class Microwave Reactor (CEM, Matthews, N.C.). The light brown solution was allowed to cool then moved to a watch glass, which was placed into a 100° C. oven for the water to slowly evaporate. The yellow and green solids (it was found that the bubbling the solution with Ar gas before reacting helped uniform the solids to yellow, although that did not improve the yield) were washed first with ethanol then acetone in a fritted filter flask. The powder was allowed to dry under vacuum overnight. Yields were approximately 30-40%. Light-yellow crystals were grown by dissolving the crude solid product in a small amount of water and layering first methanol then acetone over the solution.

Phosphorescent chitosan hydrogel nanoparticles (PCHNPs) that are highly-dispersed were synthesized at room temperature following a simple polyelectrolyte complexation (PEC) approach by simple drop-wise addition of an aqueous solution of polyanionic AuP to homogenously mix with an aqueous solution of the chitosan polymer. Formation and tunability of size and properties of the resultant phosphorescent nanogel/microgel aqueous dispersions as a function of chitosan wt %, pH, and AuP concentration was investigated.

Figure 3:
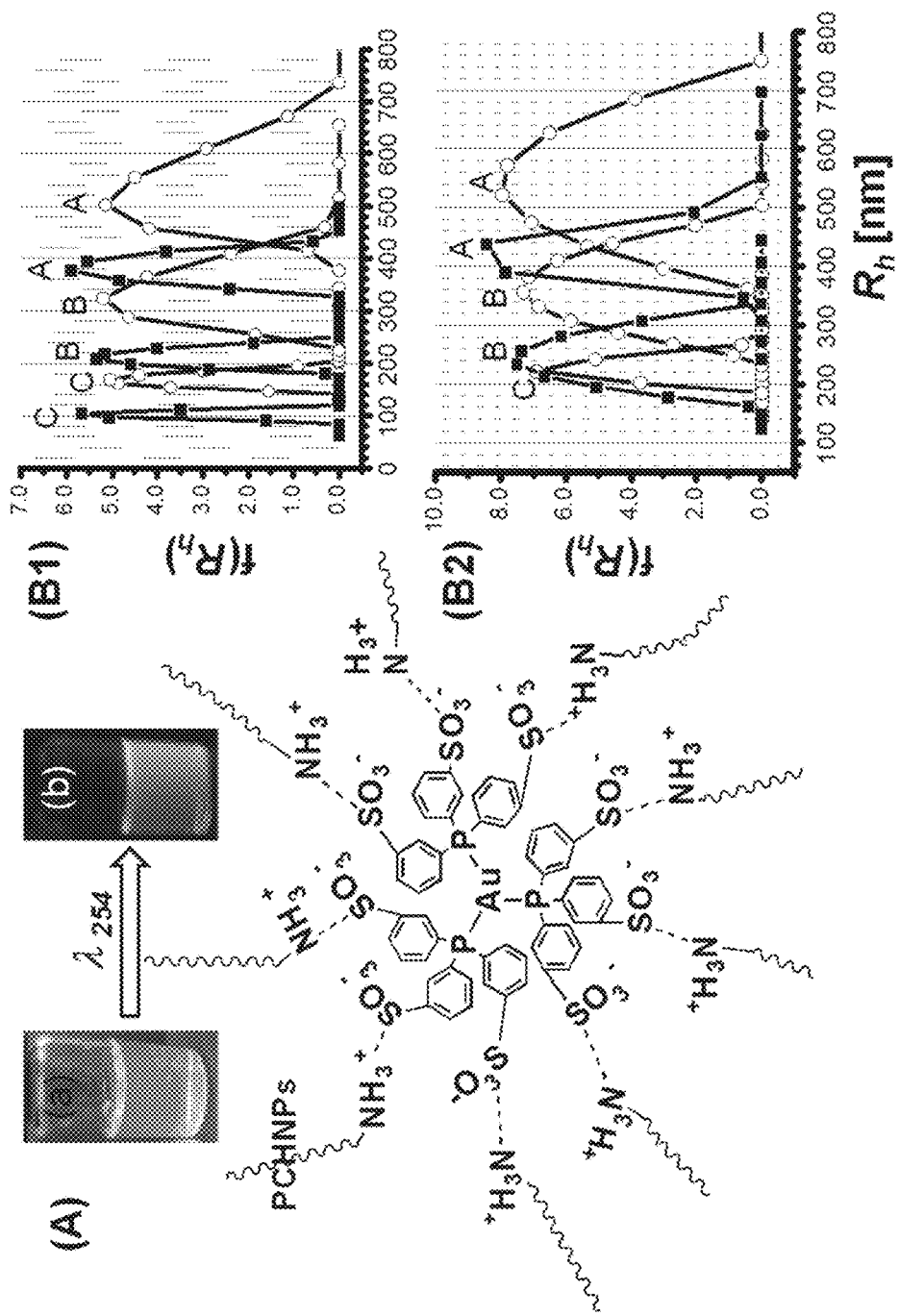
FIG. 3 shows (A) a schematic of formation of exemplary PCHNPs due to polyelectrolye interactions, and hydrodynamic radius ($R_h$) of PCHNPs measured by DLS at (B1) pH 3.0 and (B2) pH 5.0.

As depicted in FIG. 3A, polyelectrolytic interactions between the protonated amine groups of the chitosan polymer and anionic sulfonate groups of AuP allow for self-assembly and formation of PCHNPs. FIG. 3A shows the schematic formation of PCHNPs due to polyelectrolyte interactions between the chitosan polymer (CS) and the gold(I) phosphor (AuP). The inset shows phosphorescent chitosan hydrogel particles at room light (a) and under 254 nm UV exposure (b). Further discussion of DLS and TEM data is provided below. The nanoparticle formation mechanism in the PCHNPs herein is postulated to be similar to the PEC mechanism known for other polyelectrolyte cross-linkers, such as tripolyphosphate (TPP) and dextran sulfate (DS). More specifically, the mechanism for the formation of PCHNPs most closely resembles that for particles formed using DS because of the presence of sulfonate groups in both polyelectrolytes. Size could be varied systematically and rather easily based on reaction conditions upon mixing of chitosan with AuP without the addition of other cross-linkers or surfactants.

Figure 5:
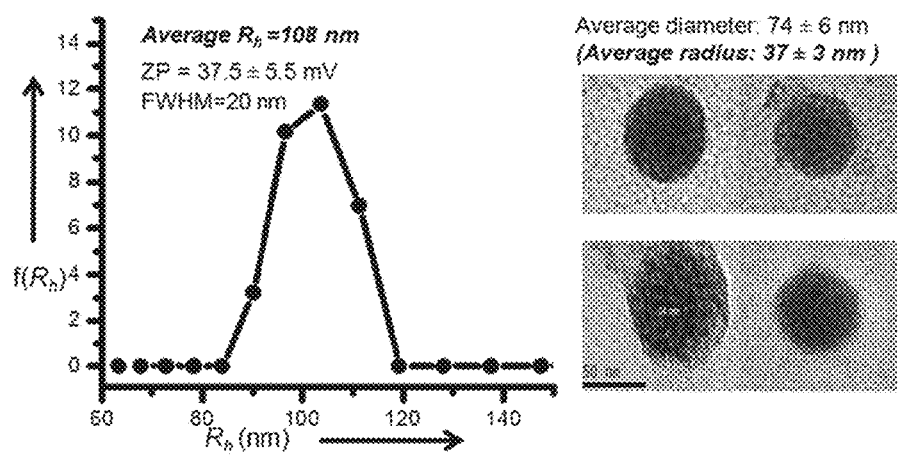
FIG. 5 shows DLS data and corresponding TEM images for PCHNPs made using 5 mM AuP concentration and pH 3.0 with (A) 0.05 wt % chitosan and (B) 0.1 wt % chitosan.
Figure 5:
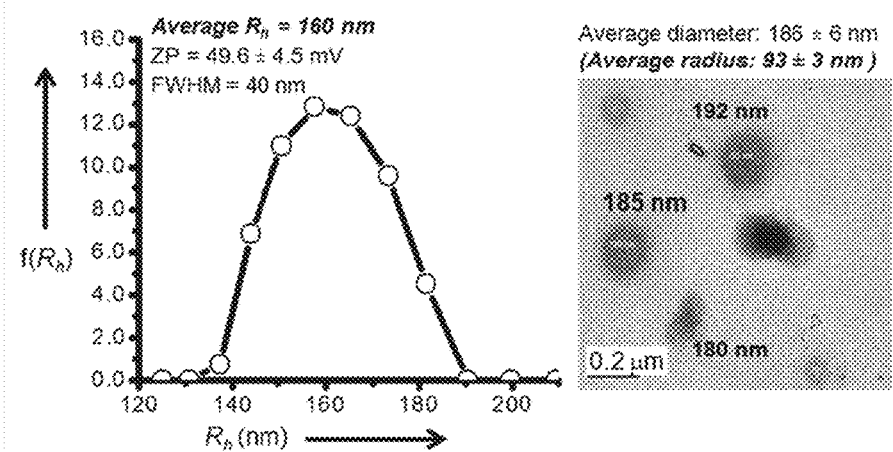
Figure 6:
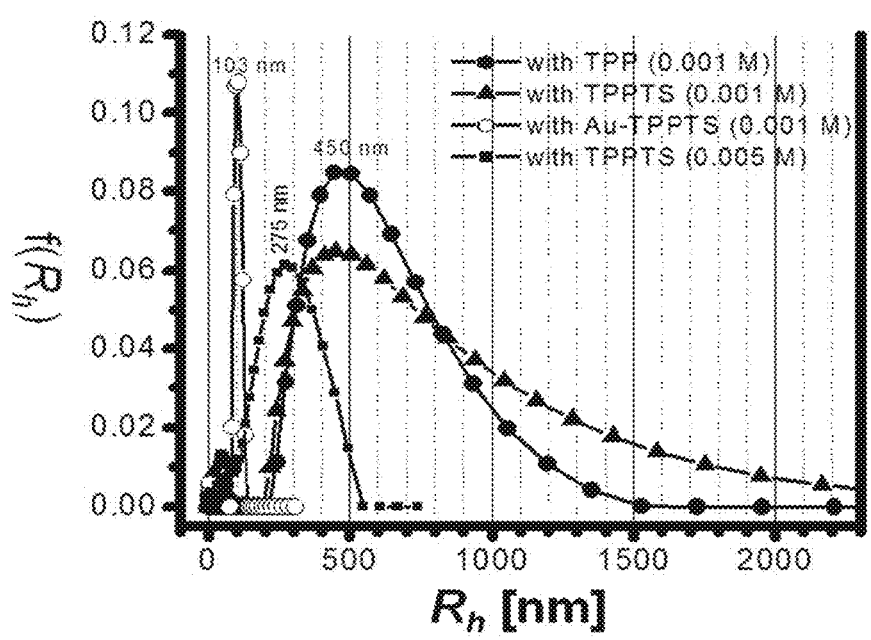
FIG. 6 shows hydrodynamic radius ($R_h$) of PCHNPs prepared by different physical cross-linking agents at different concentrations.

Additional experiments were performed to contrast the effectiveness of the PEC cross-linking in the PCHNPs herein using AuP versus that effected by non-luminescent reagents. FIG. 5 shows DLS data and corresponding TEM images for PCHNPs made using 5 mM AuP concentration and pH 3.0 with (A) 0.05 wt % chitosan and (B) 0.1 wt % chitosan. Note the smaller average radius values in the TEM images than the corresponding values ($R_h$) in the DLS data. FIG. 6 shows dynamic light scattering data obtained to compare $R_h$ (hydrodynamic radius) values for chitosan particles formed using similar molar concentrations of AuP, TPPTS and TPP. Hydrodynamic radius ($R_h$) of PCHNPs prepared by different cross-linking agents (AuP vs. TPPTS vs. TPP) at different concentrations (TPPTS: 3,3',3"-Phosphanetriyltris(benzenesulfonic acid) trisodium salt; TPP: Tripolyphosphate) is shown. These data demonstrate cooperative cross-linking due to simultaneous action of three TPPTS groups in the polyanionic AuP complex, which yields smaller particles with better (narrower) size distribution than those obtained with more than 3× the amount of free TPPTS. The findings based upon the data shown in FIG. 6 likewise suggest that the AuP phosphor is a better physical cross-linker than the more common TPP reagent.

Example 3. Formation and Stability

Analysis of Effect of Various Parameters on Formation and Stability of PCHNPs.

Formation, size, and distribution of phosphorescent chitosan hydrogel nanoparticles were analyzed by light scattering studies. FIG. 3B shows dynamic light scattering (DLS) data for PCHNPs synthesized under a variety of reaction conditions where the average hydrodynamic radius ($R_h$) and particle distribution exhibited a direct dependence on chitosan polymer wt %, AuP molar concentration, and pH. FIG. 3B shows hydrodynamic radius ($R_h$) of PCHNPs measured by DLS, with (B1): pH 3.0, (B2): pH 5.0, open circles: 0.1 wt % chitosan, filled squares: 0.05 wt % chitosan, and [AuP]/mM: (A) 0.5; (B) 1; (C) 5. Smaller particles and narrower particle distributions (optimum particle characteristics) were obtained at higher AuP concentrations, lower chitosan wt %, and lower pH (FIG. 3B and Table 1). Table 1 below summarizes in detail the variations in particle size, distribution and zeta potential values of PCHNPs synthesized under different experimental conditions.

TABLE 1

| CS wt % | 0.1 | | 0.05 | |
|---|---|---|---|---|
| pH (ZP of CS) | 3.0 | 5.0 | 3.0 | 5.0 |
| | (+62.5 ± 6.6 mV) | (+45.4 ± 5.4 mV) | (+53.8 ± 5.9 mV) | (+30.8 ± 4.7 mV) |

TABLE 1-continued

| [AuP] (mM) | 0.5 | 1.0 | 5 | 0.5 | 1 | 5 | 0.5 | 1 | 5 | 0.5 | 1 | 5 |
|---|---|---|---|---|---|---|---|---|---|---|---|---|
| $R_h$ (nm) | 518 ± 19 | 305 ± 15 | 160 ± 9 | 544 ± 21 | 352 ± 16 | 210 ± 10 | 384 ± 15 | 219 ± 9 | 108 ± 6 | 420 ± 17 | 246 ± 13 | ppt |
| ZP (+mV) | 55.6 ± 6.8 | 51.9 ± 5.5 | 47.5 ± 4.9 | 38.6 ± 6.3 | 34.9 ± 6.1 | 30.5 ± 4.4 | 46.4 ± 4.9 | 42.8 ± 4 | 39.5 ± 4 | 22.3 ± 4 | 16 ± 4 | 10.4 ± 4 |
| PDI | 0.32 | 0.18 | 0.08 | 0.31 | 0.24 | 0.11 | 0.19 | 0.09 | 0.04 | 0.22 | 0.23 | ppt |
| FWHM (nm) | 183 | 135 | 40 | 261 | 165 | 85 | 72 | 48 | 20 | 107 | 120 | ppt |

Table entries above illustrate the interdependency of three factors—chitosan (CS) wt %, AuP concentration and pH of the medium—on tuning the average size, particle distribution, and surface charge of PCHNPs. The data illustrate how the average hydrodynamic radius ($R_h$) and zeta potential (ZP) of PCHNPs will change with respective changes in different experimental parameters during the syntheses. Standard deviations for $R_h$ and ZP were computed based on three experimental values. Polydispersity index (PDI) and full width at half maximum (FWHM) values relate to DLS curves of PCHNP samples obtained during $R_h$ measurements of aqueous dispersions.

Figure 4:
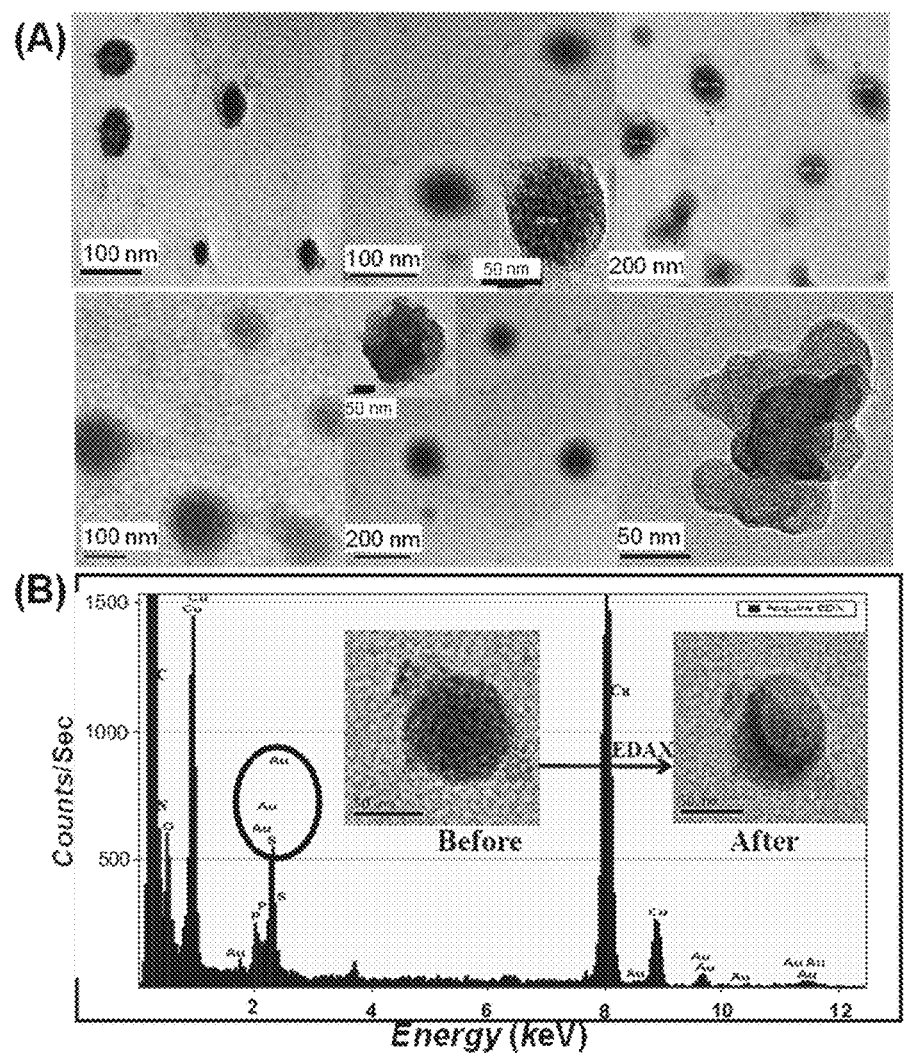
FIG. 4 shows (A) TEM images of PCHNPs at various synthetic conditions whereby the polyanionic AuP is acting as a contrast agent and (B) EDX spectrum for typical PCHNPs.

A step-wise increase in AuP concentration from 0.5 to 5 mM results in a sharp decrease in $R_h$ from 384±15 nm to 108±6 nm (FIG. 3B and Table 1). Further increase in AuP concentration beyond the critical concentration of 5 mM, however, results in particle agglomeration, whereas any concentration lower than 0.5 mM does not result in formation of particles due to lack of sufficient interactions between chitosan and AuP. The changes in size correlated with variations in zeta potential values, which exhibit a significant decrease from +53.8±5.9 mV for the chitosan polymer alone to +39.5±4.5 mV for the 108±6 nm PCHNPs, indicating partial neutralization or decrease in surface positive charge of the chitosan polymer on interacting with polyanionic AuP species. These size trends are also verifiable by TEM, which shows decreasing average diameter of PCHNPs from 160 nm to 40 nm (FIG. 4). FIG. 4A shows TEM images of PCHNPs vs. synthetic conditions: (a)-(c) 0.05 wt % chitosan, pH 3.0, [AuP]/mM=7 (a); 5 (b); 1 (c). (d)-(e) 5 mM AuP, 0.1 wt % chitosan, pH=3.0 (d); 5.0 (e), (f) 0.05 wt % chitosan, 5 mM AuP, pH 5.0. Arrows point at selected particles showing non-uniform edges to underscore the amorphous polymeric nature of PCHNPs. FIG. 4B shows EDX spectrum for typical PCHNPs. Inset shows changes in nanoparticle morphology before and after electron irradiation during EDX analysis. Black circles show significant Au peaks indicating the presence of gold from AuP. The Cu peaks are from the sample grid.

The decrease in size and zeta potential due to increased cross-linking density at higher polyanionic cross-linker concentration is well-understood. The DLS data also show that PCHNPs exhibit a reduction in $R_h$ from 160±9 nm to 108±6 nm upon decreasing chitosan polymer concentration from 0.1 to 0.05 wt % at pH 3.0 (FIG. 2B and Table 1). This trend is also substantiated by TEM (FIG. 4A(b) vs. FIG. 4A(d)) and is in agreement with literature precedents showing formation of smaller particles due to decreased number of polymer chains dispersed in solution.

At concentrations below 0.05 wt % chitosan, particles did not form, most likely due to insufficient surface charge, as indicated by zeta potential data from Table 1. As for pH effects, studies were performed at two pH values (pH 3.0 and 5.0) below the pKa (~6.5) for the chitosan polymer. Significant differences in the average sizes and distributions of PCHNPs were observed (FIGS. 3B and 4; Table 1). Using 0.1 wt % chitosan, a consistent decrease in $R_h$ was observed as the pH was reduced from pH 5.0 to pH 3.0 (by 5%, 14% and 20% for three different AuP concentrations; Table 1). Higher chitosan charge at lower pH most likely leads to enhanced interactions with the $[Au(TPPTS)_3]^8$ polyanions, resulting in a decrease in size, which has been observed by others. Significant differences in size and dispersity are also observed by TEM. Smaller and more disperse particles are obtained at pH 3.0 (FIG. 4A(d)) while larger PCHNPs that are more prone to agglomeration are obtained at pH 5.0 (FIG. 4A(e)). This tendency toward agglomeration was highest in particles synthesized at higher AuP concentration (5 mM), lower chitosan wt % (0.05), and higher pH (5.0), illustrated in FIG. 4A(f), due to surface charge and polyanionic interaction effects. Light scattering data also suggest that the ionic strength affects the size, size distribution, and stability of PCHNPs. In aggregate, the results suggest that a critical combination of AuP concentration, pH, chitosan wt %, and ionic strength is required for balancing electrostatic interactions in order to form stable aqueous dispersions of PCHNPs.

Example 4. Characterization by Electron Microscopy

Characterization of PCHNPs by Electron Microscopy.

The presence of AuP in PCHNPs also provides sufficient contrast for electron microscopy to be conducted on samples without the need for additional contrast agents. The non-uniform amorphous structure observed in TEM images of PCHNPs confirm their polymeric nature. Some apparent discrepancy in average size obtained from DLS vs. TEM data is observed for identical samples (compare values from FIG. 4; Table 1), which is common for hydrogel particles. For comparison, PCHNPs obtained from a combination of 0.05 wt % CS/pH 3.0/5 mM AuP attain $R_h$=108±6 nm in solution using light scattering technique, whereas the same sample analyzed by TEM in the dried state exhibits particles 90±7 nm in diameter. The same trend, nevertheless, is observed for all particles analyzed (FIG. 4 and Table 1). This discrepancy can be attributed to the hydrophilic nature of PCHNPs, which swell in aqueous media due to the presence of polyelectrolytic species. However, the colloidal stability of PCHNPs is evident from both light scattering and TEM data. TEM images of particles that were synthesized at pH 5.0 suggest that they exhibit more particle agglomeration compared to particles at pH 3.0, which is consistent with polydispersity data from DLS.

Qualitatively TEM and light scattering data are in agreement, showing significant effects of pH on the stability and dispersity of the particles. FIG. 4B shows that distinct signals for carbon, nitrogen, phosphorus, sulfur, and gold atoms are observed by EDX (electron dispersive X-ray) spectroscopy, in agreement with known energy dispersive X-ray lines (Au: 9.71 and 2.12 keV; S: 2.30 keV; P: 2.01 keV; O: 0.52 keV; Cu: 8.04 and 0.92 keV; C: 0.28 keV). TEM images obtained in combination with EDX analysis (FIG. 4B) show significant degradation of PCHNPs upon exposure to an electron beam, which confirms the polymeric nature of the particles.

Example 5. Photoluminescence Features

Photoluminescence Features of Phosphorescent Self-Assembly Systems.

Figure 7:
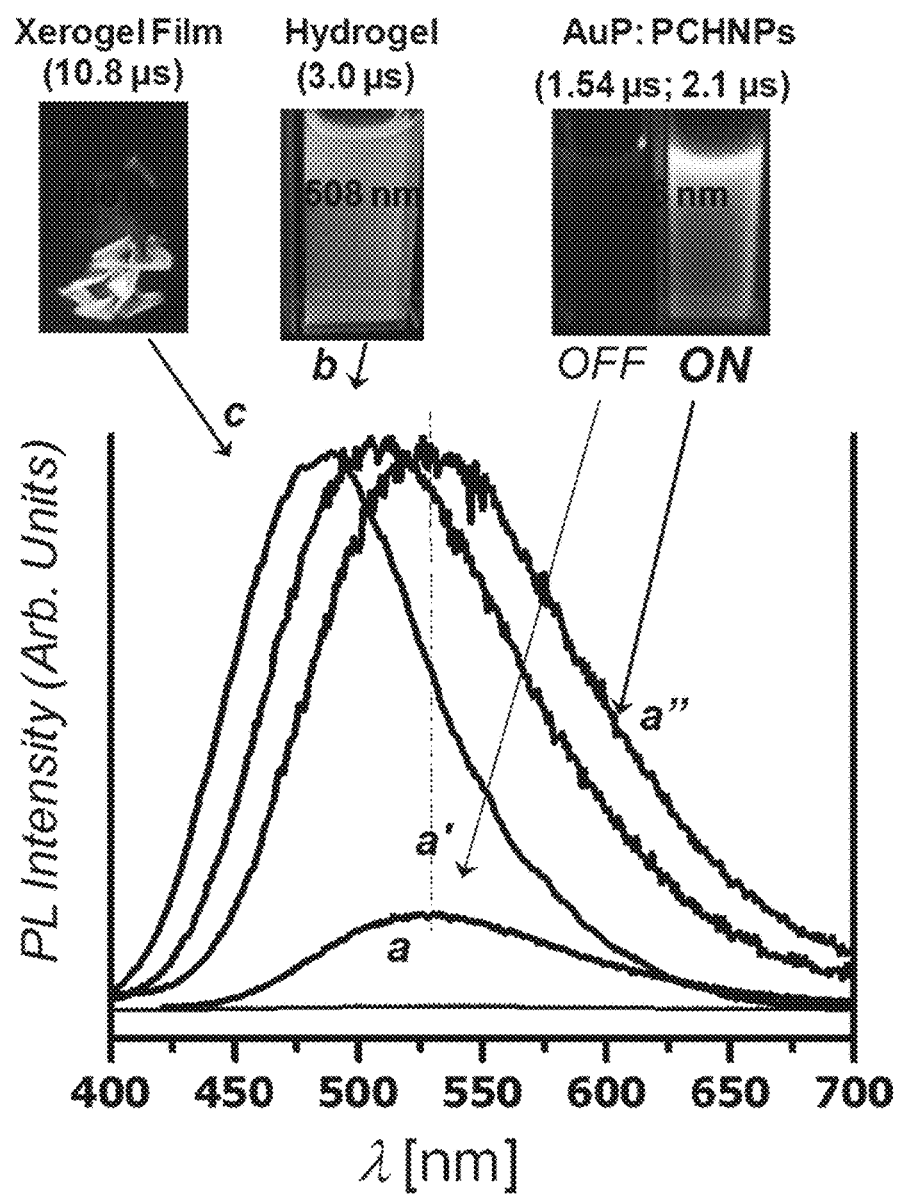
FIG. 7 shows photoluminescence (PL) changes for three AuP/Chitosan sample forms with sensitized PL vs. AuP/$H_2O$.
Figure 8:
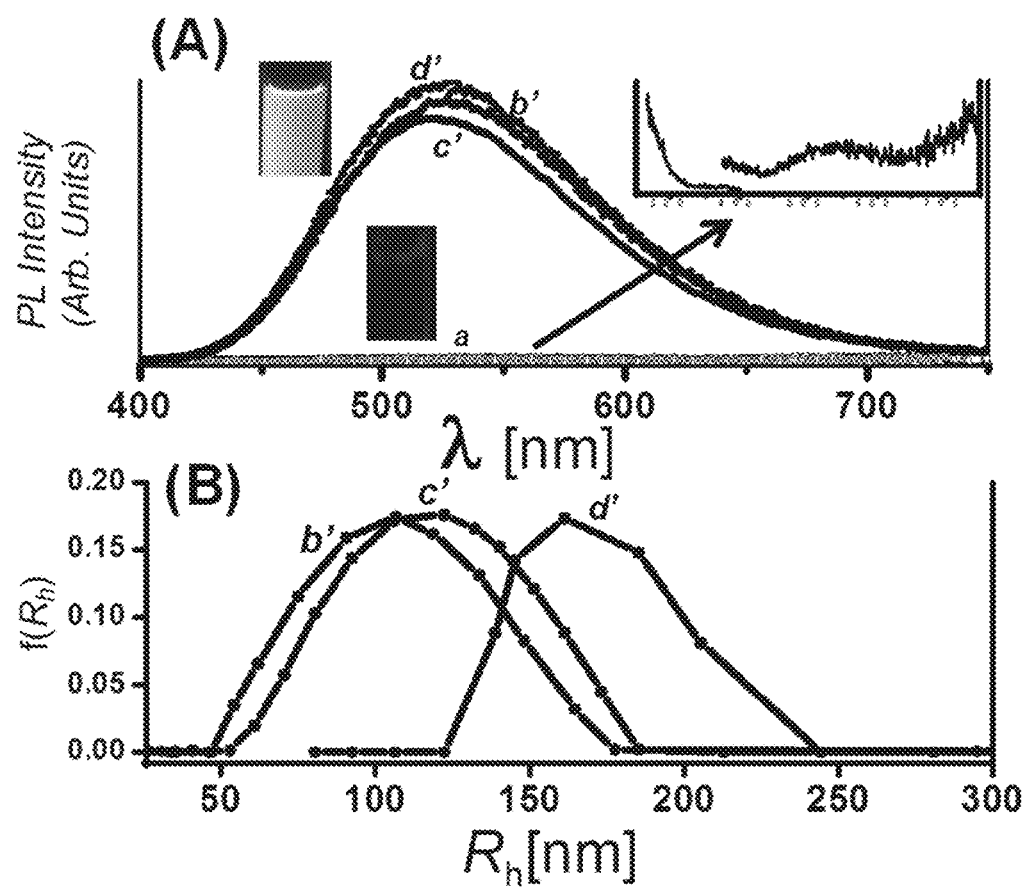
FIG. 8 shows (A) relative PL sensitization of AuP in different polymer media vs. a polymer-free aqueous solution and (B) hydrodynamic radius ($R_h$) data of AuP/Polymer polyelectrolyte hybrids.

The work herein shows that biocompatible linear polymers can attain nanoparticles with greatly-sensitized phosphorescence in an aqueous environment without the need for the phosphorescent complex to be doped in an existing polymer microsphere or nanosphere particles, as demonstrated for AuP in chitosan (FIG. 7) and several other biocompatible linear polymers (FIG. 8). This section elaborates these findings in detail for the sensitization and tuning of AuP phosphorescence in chitosan while the generalization to other biocompatible linear polymers is discussed in the subsequent section.

FIG. 7 shows photoluminescence (PL) changes for three AuP/Chitosan sample forms with sensitized PL vs. AuP/$H_2O$. The PL intensity is normalized except for the two AuP aqueous solutions whose PL intensities are plotted relative to that for dispersed PCHNPs to show the relative sensitization. Notation: a=$10^{-5}$ M AuP/$H_2O$; a'=$10^{-4}$ M AuP/$H_2O$; a"=$10^{-5}$M AuP/Chitosan; b=AuP/Chitosan in hydrogel form; c=AuP/chitosan dry film (xerogel) form. FIG. 8A shows relative PL sensitization of AuP in polymer media vs. a polymer-free aqueous solution. Notation: a=AuP/$H_2O$ (non-emissive visually); b'=AuP/Poly-L-lysine; c'=AuP/ Polyethyleneimine; d'=AuP/Poly-diallyldimethylammonium chloride. FIG. 8B shows hydrodynamic radius ($R_h$) data of AuP/Polymer polyelectrolyte hybrids. Notation: b'=AuP/Poly-L-lysine; c'=AuP/polyethyleneimine; d'=AuP/poly-diallyldimethylammonium chloride.

All different forms of the phosphorescent chitosan matrix, ranging from dispersions in aqueous media to aggregates in gel media and dry thin films, exhibited complete retention of photoluminescence (PL) features of the entrapped AuP (FIG. 7). Retention of a broad PL peak at ~520-530 nm from PCHNP dispersions after dialysis for 48 hrs confirmed the strong polyelectrolyte interactions with AuP and its retention within the chitosan matrix. Complete photoluminescence characterization of molecular AuP in different forms (aqueous vs. solid with PL maxima at ~520-530 vs. ~480-490 nm; see FIGS. 9 and 10 for details) reproduced reported results. Theoretical studies predicted a T-shaped excited state structure via photoinduced Jahn-Teller distortion, which causes solid or rigid environments around AuP to attain blue-shifted PL bands than those in solution or hydrogel environments, as demonstrated for AuP in PNIPAM hydrogel microsphere environments, akin to other phosphorescent systems that exhibit PL changes based on the viscosity or rigidity of non-aqueous polymer media. It is demonstrated herein that such tunable emissions are possible in an aqueous polymer environment (of chitosan in particular), such that AuP-chitosan aqueous hybrid composites exhibit the solid-state xerogel/thin film rigid and aqueous dispersion extremes with blue and green PL maxima at ~480-490 and 520-530 nm, respectively, as well as an intermediate situation between these two extremes with a turquoise blue-green PL color with a peak maximum at ~500-510 nm (FIG. 7).

Chitosan aqueous dispersions exhibit tunable emissions without the need for the phosphorescent complex to be doped in an existing microsphere or nanosphere polymer particle. Indeed, even in non-aqueous polymer media, the transformation of the probe molecules is usually manifest in merely the two extremes without an intermediate situation, such as the situations for organogels containing trimeric gold-pyrazolate complexes or for sol-gel silica matrices containing a variety of organic, metal complex, or biological probe chromophores. For example, cytochrome c was shown to exhibit absorption maxima that toggle between ~395 nm in a silica xerogel to ~405 nm in the corresponding aged gel, rehydrated gel, or fluid aqueous solution without a silica matrix. Similar situations existed for the electronic absorption or PL changes in non-aqueous or mixed aqueous/non-aqueous media involving all other fluorescent (e.g., deprotonated vs. protonated pyrene at 430 vs. 515 nm in propanol/water mixtures) or phosphorescent (e.g., ReCl(CO)bpy at 612 vs. 529 nm in ethanol fluid vs. frozen glassy matrices, or Ag(I)-doped cyclotrimeric Au(I)-pyrazolate adducts at 458 vs. 501 nm in hexane organogel vs. solution forms) probes. The chitosan matrix in aggregate hydrogel form possesses intermediate rigidity between that of aqueous nanoparticle dispersions and solid xerogel films, resulting in an intermediate emission centered at ~500-510 nm and an intermediate lifetime of 3.0 μs (vs. 1.5-2.1 μs for green-emitting aqueous solutions or nanoparticle dispersions and 10.8 μs for AuP-doped chitosan dry xerogel films; FIG. 7). Such a demonstration of rigidochromic tunability in aqueous media is rarely documented and propels the usage of the proposed composition for rigidity analysis in a polymer setting environment.

Furthermore, a remarkable PL enhancement of approximately 100-fold (100×) is attained for highly-dispersed PCHNPs compared to aqueous solutions of AuP alone with the same concentration; see trace (a") vs. (a) in FIG. 7 for 10 M solutions, for which the PL sensitization ration is 166× at 526 nm for (a") vs. (a), which is significantly greater than the enhancement upon a 10-fold increase in AuP concentration as shown in trace (a'). The enhancement in the dry xerogel film form is even greater in terms of both intensity and lifetime. Luminescence enhancements, albeit to a lesser extent, have been observed in other reported systems in the presence of polymer or microparticle matrices, and have been attributed to entrapment or energy transfer. However, the near-perfect on/off emission switching observed for dilute AuP solutions (sub-mM) based on the presence of chitosan, depicted in FIG. 7, is significantly more pronounced than the situation in any other known phosphorescent probe system.

Figure 11:
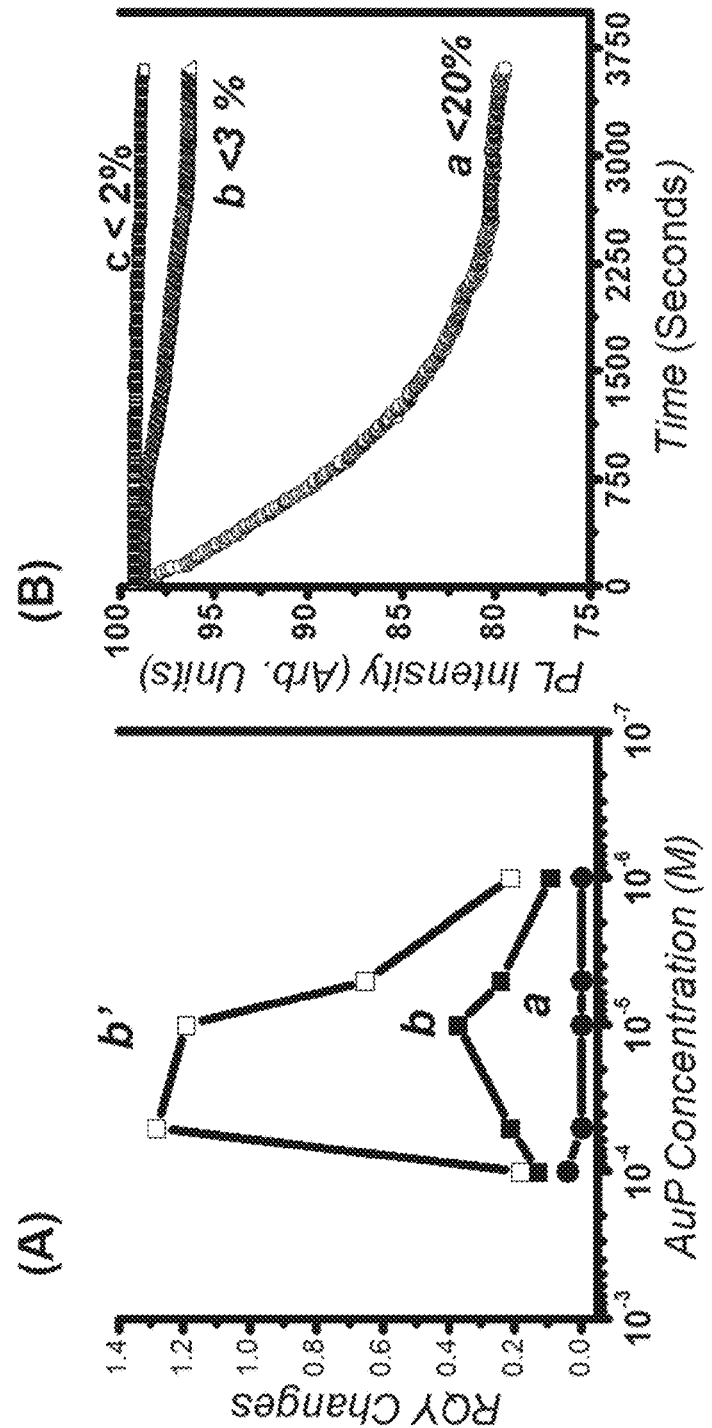
FIG. 11 shows (A) relative photoluminescence quantum yield of AuP aqueous and in the presence of chitosan at different molar concentrations of AuP vs. quinine sulfate solution (56%) and (B) photobleaching data of AuP in different forms.

Careful examination of the relative photoluminescence quantum yield (RQY) values at different molar concentrations of AuP with or without added chitosan revealed a drastic concentration-dependent sensitization in the presence of chitosan (FIG. 11A). FIG. 11A shows relative photoluminescence quantum yield of AuP aqueous and in the presence of chitosan at different molar concentrations of AuP vs. quinine sulfate solution (56%). Notation: a) AuP/$H_2O$; b) AuP/Chitosan considering scattering due to colloidal dispersions; b') AuP/Chitosan neglecting scattering due to colloidal dispersions. FIG. 11B shows photobleaching data of AuP in different forms. Notation: a=AuP/$H_2O$; b=PCHNP solution; c=dry (xerogel) thin film AuP is non-emissive visually at sub-mM concentrations in the absence of chitosan (FIG. 7). However, the corresponding PCHNP hybrid systems (containing the same AuP concentration) exhibit approximately twice the RQY compared to aqueous AuP (4%). Titration of infinitesimally small volumes (L scale) of chitosan using a micropipette to a more-than-half-full cuvette (3-4 mL) containing the aqueous AuP induces the switching between a non-luminescent and luminescent species (FIG. 7). Furthermore, a dramatic, more than two-order-of-magnitude enhancement in RQY is observed if the scattering effects due to the presence of nanoparticles is taken into consideration (assuming that the absorption of AuP in PCHNP dispersions is the same as that in aqueous AuP without chitosan). Although this unusual on/off emission sensitization is not fully understood, the non-equivalent rise in lifetime values compared to emission enhancement could be attributed to the combined effects of reduced water accessibility, polymer entrapment, stabilization, and/or increased scattering in the PCHNPs, as detailed in previous work involving zinc oxide in PNIPAM hydrogel microparticle media. The PL enhancement for PHCNPs parallels or exceeds that reported not only for chitosan but other well-established yet less-benign polymer hydrogel materials than chitosan (such as PNIPAM microspheres, organogels, or silicates/aluminosilicates) and/or more cytotoxic luminophores (such as cadmium-containing quantum dots or polycyclic aromatic hydrocarbons).

Excluding previous reports for PNIPAM/AuP and PNIPAM/ZnO systems, which showed similar order-of-magnitude PL enhancements, a CdTe/PNIPAM system was reported as showing a modest 2-5% PL enhancement. Studies have reported the synthesis of brightly-fluorescent and photostable silica particles by encapsulation of organic dye molecules. However, no phosphorescent system exhibiting such dramatic PL on/off sensitization merely due to polyelectrolyte interactions has been reported. Without being bound by theory, it is believed that, being metal-centered emission, the green AuP phosphorescence stems from the direct Au(I)—$P_3$ coordination environment whereas the usually quenching amine groups of the polymer would interact non-covalently with the sulfonate groups of the TPPTS ligands; these sulfonate and amine groups are quite far away from the Au(I)—$P_3$ coordination environment responsible for the Au-centered phosphorescence of the AuP complex.

Along with the RQY enhancement, an order-of-magnitude increase in the photostability of the AuP hybrid system (FIG. 11B) is observed compared to AuP in aqueous solution, which clearly indicates that interactions following entrapment of AuP within chitosan polymers lead to enhanced stability. There has been a great deal of interest in enhancing the photostability of luminophores in a variety of applications, as typical organic chromophores in particular (including metal-organic complexes) are usually notorious for their proneness to photobleaching. The present disclosure represents a very simple method for enhancing the photostability of ionic molecular luminophores through proper selection of oppositely-charged polymer systems. As in the aforementioned reasoning for enhanced PL signal, the enhanced photostability of AuP is likely related to the Au-centered phosphorescence of the AuP complex such that the localization of exciton density on the Au(I)—$P_3$ coordination environment, as opposed to the aromatic moieties, would ameliorate photobleaching in a manner akin to the greater stability known for binary inorganic semiconductors than organic counterparts.

Example 6. Photoluminescence Sensing

Photoluminescence Sensing of Amine-Based Polymers.
Sensing volatile amines and also chiral amines is an important area of research both for industrial and pharmaceutical applications. Active materials for such sensors are carboxylate-based fluorescent systems or pH sensitive dyes. While amine polymers are categorically preferred for pH and $CO_2$ sensors, coatings for such applications selectively use amine-based hydrophilic polymers. It was unclear whether PL enhancement would be observed in other AuP-cross-linked phosphorescent systems. The reaction of AuP with two polymer-transfection agents (polyethyleneimine, PEI, and poly-L-lysine, PLL) and polydiallyl dimethylammonium chloride (PDADMAC) was investigated. PLL and PEI are known to interact with DNA, and PLL is well-known for its cell adhesion and in food preservative applications, whereas PEI is also well-known for usage in $CO_2$ capture. PDADMAC, another homopolymer and strong polycation has well-established usage for water purification and flocculation purposes.

Compared to the non-emissive AuP solution at micromolar concentrations, addition of any of the aforementioned positively-charged polymers at wt %<0.002 (lower than 20 ppm) spontaneously resulted in the formation of self-assembled brightly-phosphorescent colloidal dispersions. The polymers studied could be selectively differentiated based on concentration; PDADMAC could be identified at wt %≤0.002 and PLL at concentrations≤0.0001 wt %. Formation of particles was confirmed by light scattering (FIG. 8B) and the observed emission enhancements (FIG. 8A) convincingly demonstrated the sensing potential of AuP for positively-charged amine-based polymers. On/off photoluminescence emission sensitivity in response to oxygen, pH, heavy metals, due to structural changes, and intercalating to oligonucleotides have been thoroughly investigated for sensing applications. The present results represent the first demonstration of materials exhibiting on/off emission response due to polyelectrolyte self-assembly of positively-charged amine-based linear polymers in the presence of a polyanionic phosphor system. Although the phenomenon of PL enhancement has been selective with the amine-containing polymers investigated, other factors, such as polymer backbone, weight percentage, and surface charge, may have some involvement in the dramatic PL enhancements observed. A luminescence-based sensor material with the capability to distinguish between specific amine-based polymers from a mixture could be developed, which would build a valuable base for developing the next generation of sensing tools.

Figure 9:
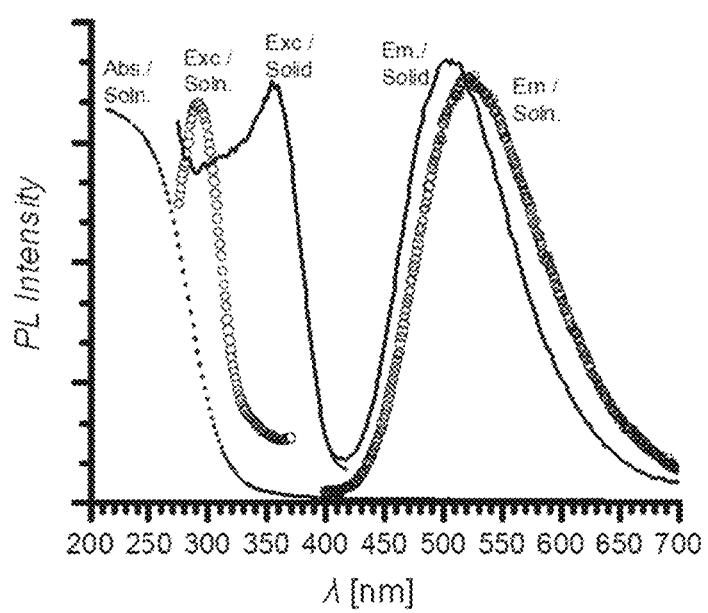
FIG. 9 shows electronic spectra (absorption and photoluminescence emission and excitation spectra) for a polyionic $Na_8[Au(TPPTS)_3]$ sample used for making PCHNPs.
Figure 10:
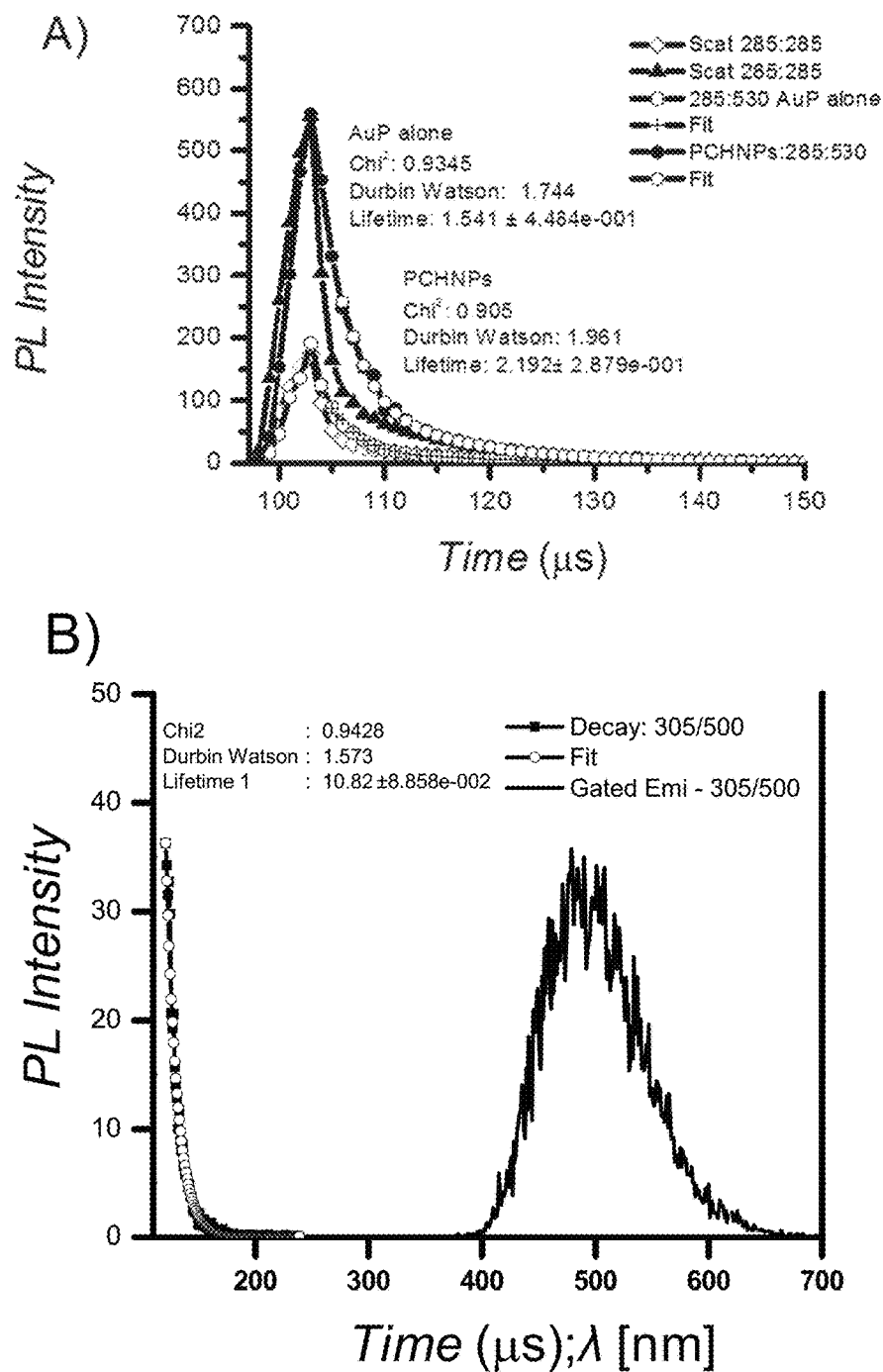
FIG. 10 shows time-resolved photoluminescence decay data using a xenon flash lamp ($\lambda_{exc}$ 285 nm) and a gated microsecond detector of (A) polyionic AuP, PCHNPs aqueous solutions and (B) PCHNP film ($\lambda_{exc}$ 305 nm).

FIG. 9 shows electronic spectra (absorption and photoluminescence emission and excitation spectra) for a $Na_8[Au(TPPTS)_3]$ sample used for making PCHNPs. The spectra for both the solid and aqueous solution are in good agreement with the literature. FIG. 10 shows time-resolved photoluminescence decay data using a xenon flash lamp ($\lambda_{exc}$ 285 nm) and a gated microsecond detector of (A) AuP, PCHNPs aqueous solutions and (B) PCHNP film ($\lambda_{exc}$ 305 nm). Also shown are scatterer decay curves used for deconvolution, as acquired while monitoring the emission at the same excitation wavelength and using the same instrumentation conditions as those for the samples.

Example 7. Emissive Chitosan Films

Figure 12:
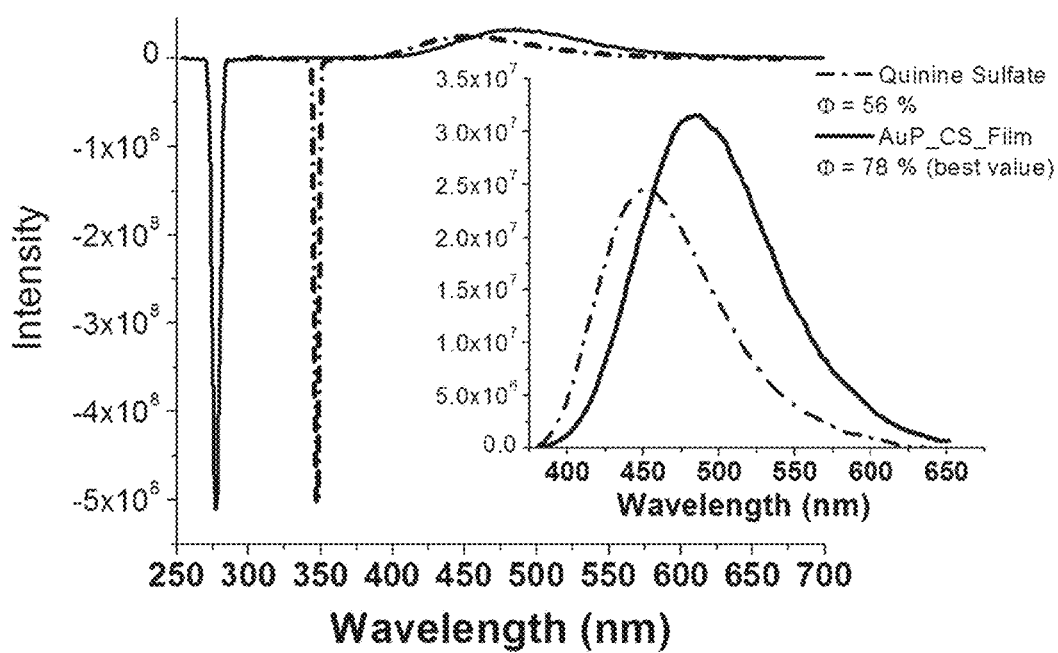
FIG. 12 shows absolute photoluminescence quantum yield of AuP/CS drop-cast film in comparison with freshly prepared standard quinine sulfate solution under similar experimental conditions.
Figure 13:
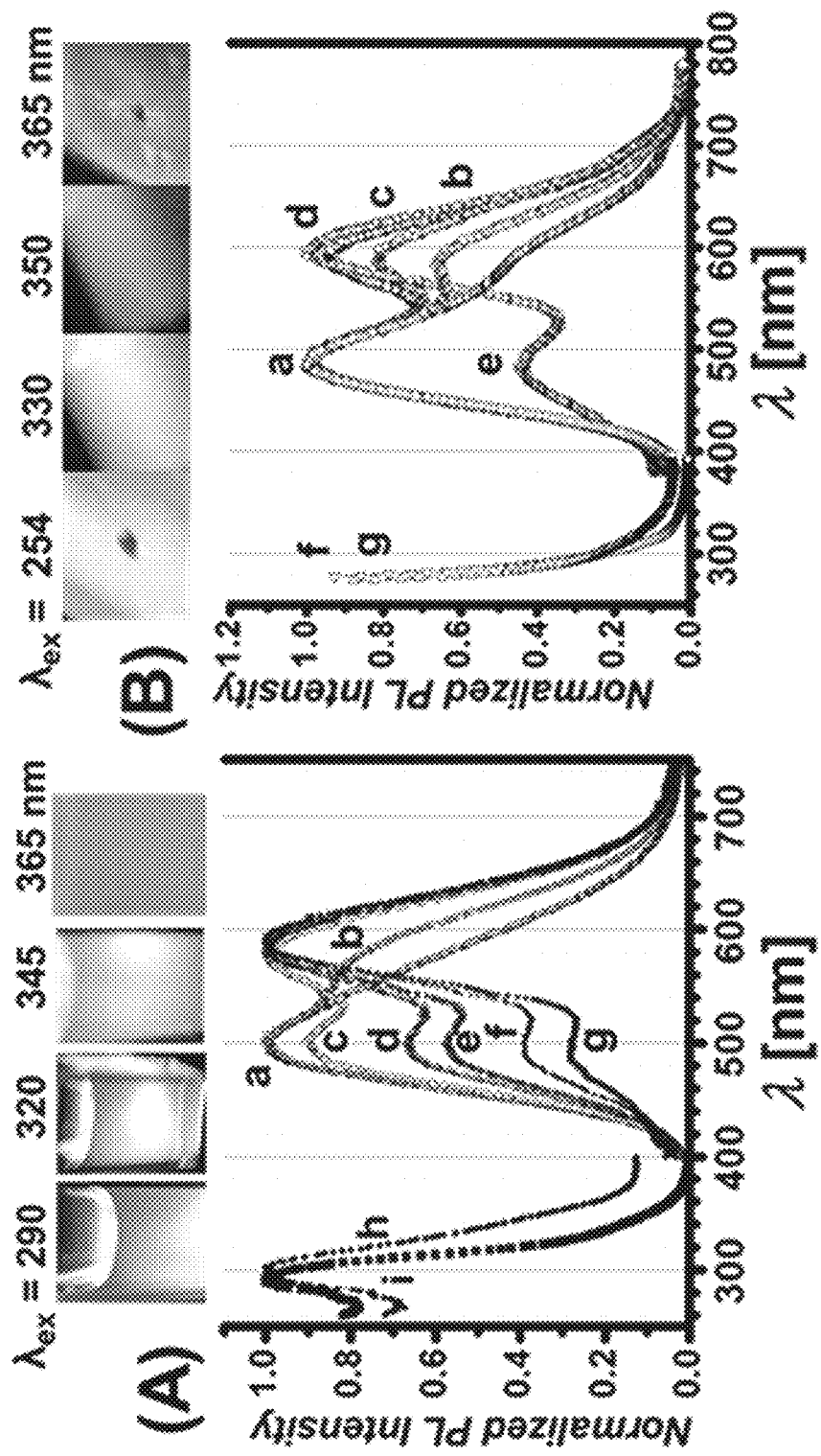
FIG. 13 shows photoluminescence data showing the formation of stable hybrid AuP—PtP systems with tunable emission spectra in (A) solution form and (B) thin-film form.
Figure 14:
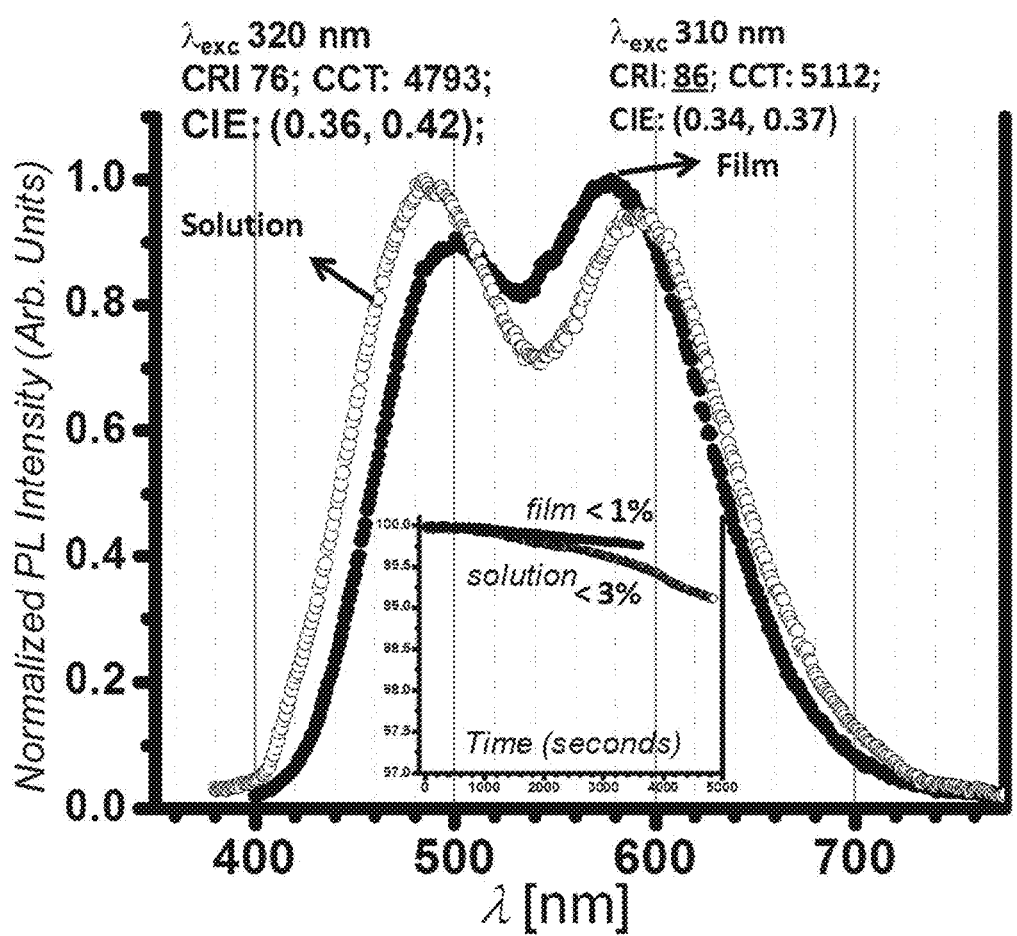
FIG. 14 shows photoluminescence data for a hybrid AuP—PtP composition that exhibits white phosphorescence in solution and thin film forms.

Blue- and White-Emissive Chitosan Films.
The film-forming ability of chitosan, extensively exploited for a variety of technologies and applications, is utilized here to demonstrate a facile method for the formation of highly-stable/brightly-phosphorescent chitosan films (FIGS. 7 and 11-14). FIG. 12 shows absolute photoluminescence quantum yield of AuP/CS drop-cast film in comparison with freshly prepared standard quinine sulfate solution under similar experimental conditions, where (a) Quinine sulfate solution, quantum yield=56%; (b) AuP/CS film, highest quantum yield=59.2±2.7% for four positions; Trial-1: Shape of film is rectangular; and Trial-2: Shape of film is square. FIG. 13 shows photoluminescence data showing the formation of stable hybrid AuP—PtP systems with tunable emission spectra. In FIG. 13A: Solution form: Emission spectra are shown with $\lambda_{ex}$=290, 310, 330, 340, 350, and 365 nm in a-g, respectively while the excitation spectra are shown with $\lambda_{em}$=500 and 580 nm in h and i, respectively. Inset shows pictures at different excitation wavelengths. In FIG. 13B: Thin-film form: Emission spectra are shown with $\lambda_{ex}$=290, 310, 330, 340, 350, and 365 nm in a-e, respectively while the excitation spectra are shown with $\lambda_{em}$=500 and 580 nm in f and g, respectively. Inset shows pictures of the emission taken at different excitation wavelengths. FIG. 14 shows photoluminescence data for a hybrid AuP—PtP system that exhibits white phosphorescence in solution and thin film forms. Calculated white color metrics are indicated for both film and solution forms. Inset shows quantitative photobleaching data for the solution and film forms of hybrid AuP—PtP systems.

Remarkably-high photochemical stability is demonstrated by the AuP-chitosan phosphorescent films, attaining infinitesimally negligible photobleaching of <2% upon continuous UV irradiation for 2 hours (FIG. 11B, trace c). The films are also stable for more than one year of storage under ambient laboratory conditions, retaining their bright blue phosphorescence (480-490 nm) with microsecond lifetimes and exhibiting remarkably-high absolute quantum yields up to 78% (duplicate experiments attained 58.9%±15.6% and 59.2%±2.7%; see FIG. 12). These are excellent optical properties for electro-phosphorescent OLEDs, for which stable blue phosphors remain the technology's weakest link toward manufacturing of solid-state light sources.

The enhanced photostability and quantum yield of AuP phosphor encapsulated within the passive chitosan matrix and the ability to form stable films from chitosan were exploited to demonstrate the formation of white-phosphorescent films by varying the doping concentrations of a blue/turquoise phosphor, AuP, in combination with a yellow/orange phosphor, Pt(ptp)$_2$ phosphor (PtP). While the syntheses and photophysical properties of PtP have been discussed elsewhere, a near-unity quantum yield was observed for PtP in combination with AuP, which also exhibited tunable emission by varying the ratio of phosphors or excitation wavelength. This technique of utilizing a chitosan matrix not only improves photostability (FIG. 14 inset) but also increases the solubility of PtP in aqueous media with complete retention of its PL properties. FIG. 13A-B shows a characteristic hybrid mixture that exhibits tunable emission from turquoise to orange both in solution and film form. The observation of white phosphorescence with high quantum yield and negligible photobleaching is useful not only for biological imaging but also lighting applications, as down-conversion phosphors for LEDs and compact fluorescent lamps (CFLs) or as emissive layers in OLEDs. Different white color metrics are given in FIG. 14 to characterize the quality of the white PL color in AuP/PtP-chitosan hybrid systems. For example, the color-correlated temperature (CCT) can be tuned from warm-white (low CCT, <5000) to cool-white (high CCT, >5000) while the color-rendering index (CRI) that measures the color quality of lit objects is shown to attain the desired values of >75 needed for most lighting applications.

Example 8. Cytotoxicity

Figure 15:
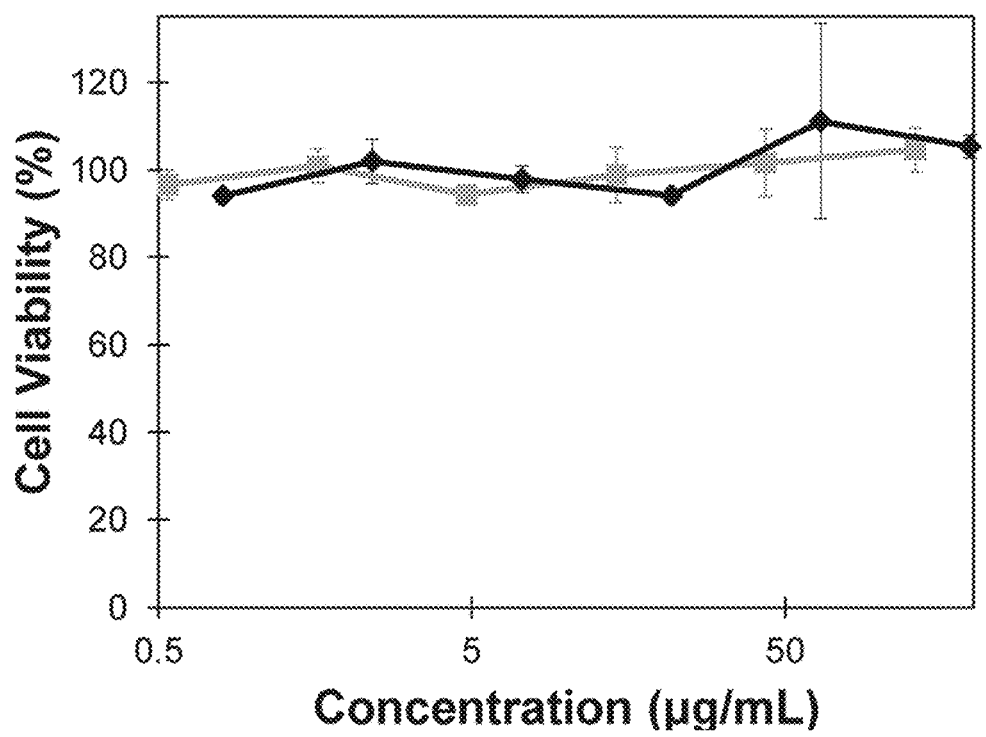
FIG. 15 shows MTT assay data for demonstrating the benign properties of AuP and TPPTS separately in SNU-5 cell lines.

Cytotoxicity Studies of PCHNPs.
Though the biocompatibility of chitosan has been well established, the biocompatibility of PCHNPs in vitro in SNU-5 cells (an immortalized gastric carcinoma cell line) was examined in order to investigate whether the embedded AuP complex causes any cytotoxicity. Cells were grown to ~90% confluence in 96 well plate format in complete growth media containing 10% fetal bovine serum. PCHNPs or TPPTs in 0.1 wt % chitosan were dosed on cells at concentrations ranging from 0.5 to 200 μg/mL. Viability after 24 h of exposure was evaluated using MTT reagent and compared to healthy cells on the same plate. FIG. 15 shows MTT assay data for demonstrating the benign properties of AuP and TPPTS separately in SNU-5 cell lines to understand biological toxicity. Black and gray traces indicate TPPTS and AuP buffered aqueous solution, respectively. No toxicity was observed up to the highest PCHNPs concentration investigated (FIG. 15), which is higher than the concentration expected to be necessary for bioimaging applications. Thus, PCHNPs are herein deemed highly biocompatible in SNU-5 cells, making PCHNPs attractive as a potential bioimaging modality.

Example 9. Hypoxia Sensing

Figure 16:
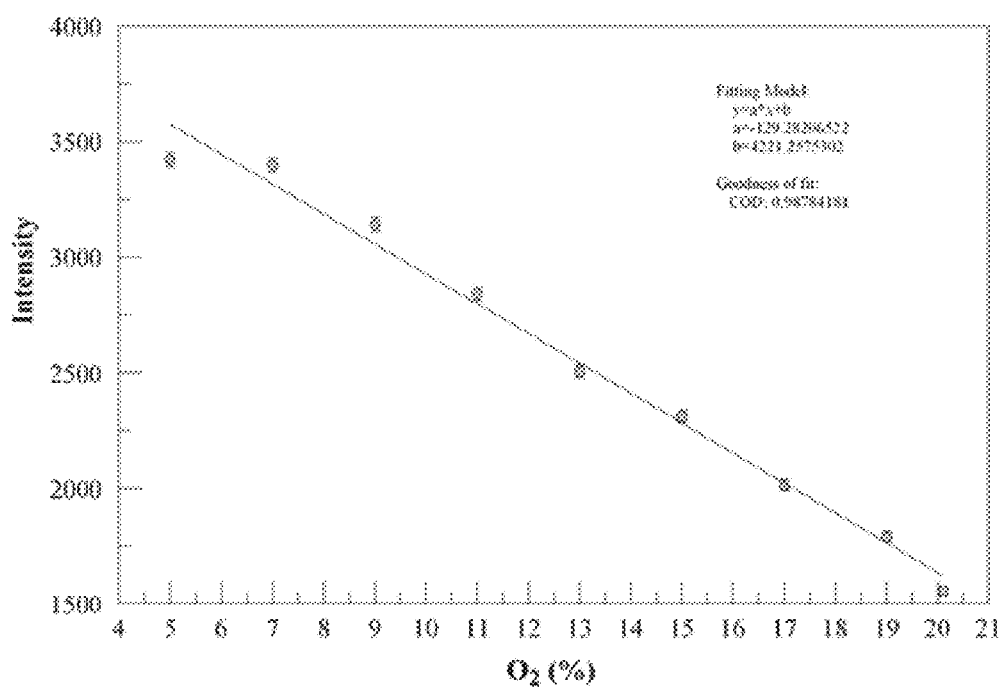
FIG. 16 shows phosphorescence intensity signal versus oxygen level for a Pt—POP aqueous solution.
Figure 17:
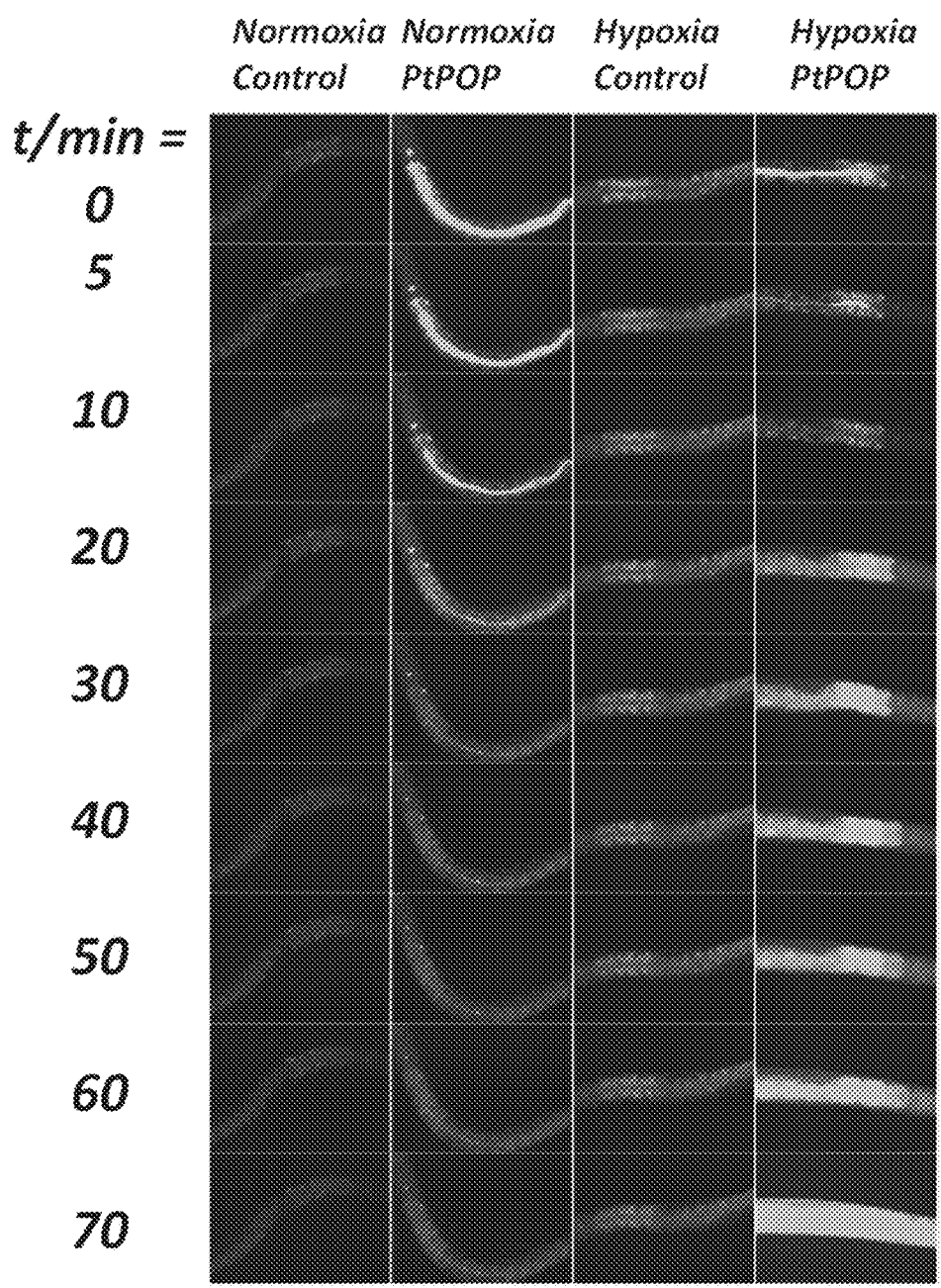
FIG. 17 shows epi-fluorescence microscopy images over time for a C. elegans worm model under normoxia and hypoxia with and without Pt—POP.
Figure 18:
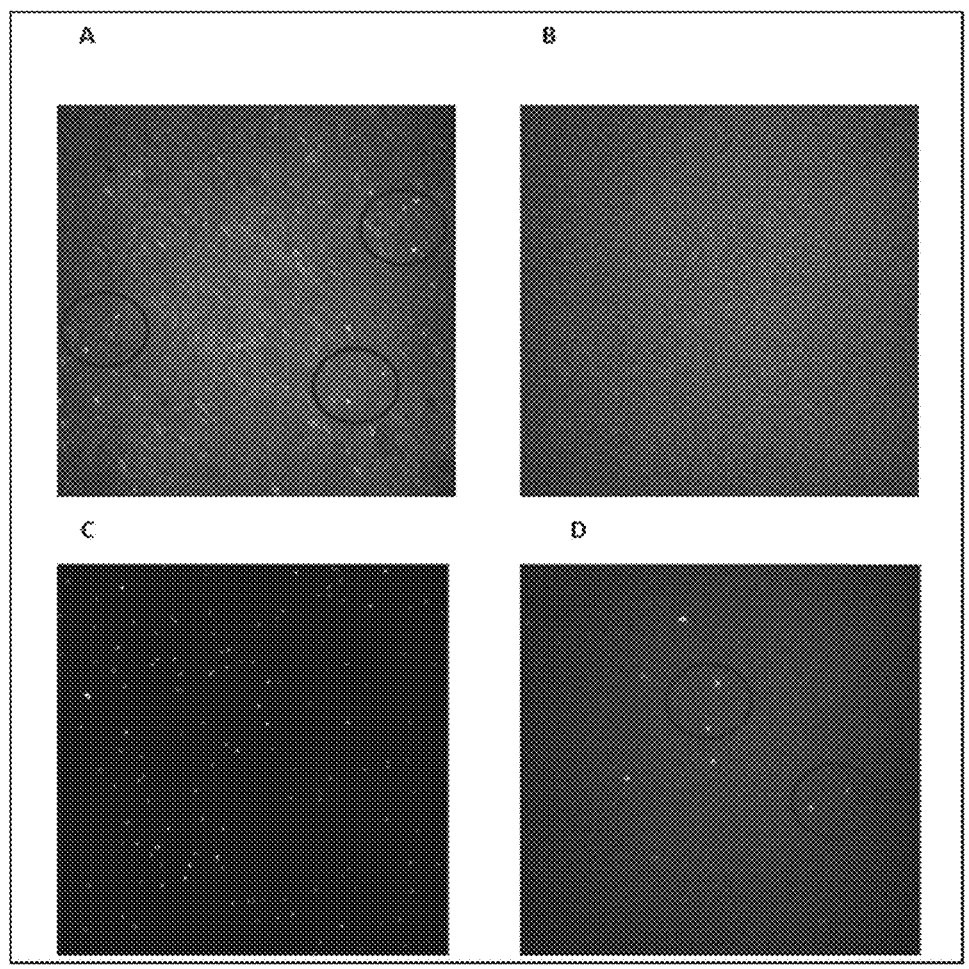
FIG. 18 shows epi-fluorescence microscopy images for a E. coli bacterium model under different conditions with and without Pt—POP.
Figure 19:
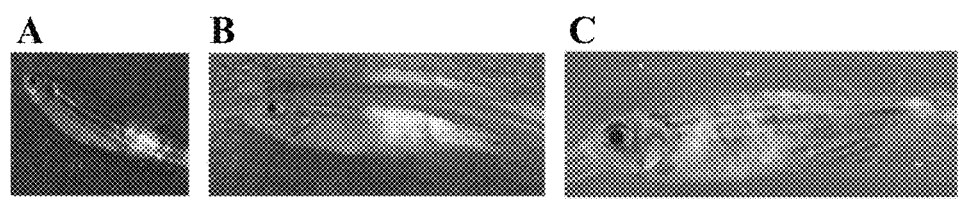
FIG. 19 shows epi-fluorescence microscopy images of a D. rerio zebra fish model (A) after injection, (B) 7 minutes after induced hypoxia, and (C) for a swimming fish.

For identification of hypoxic environments, Pt—POP has been used. The efficiency of Pt—POP as an oxygen sensor is shown in FIG. 16, including its effective usage for live bioimaging applications. FIG. 16 shows a demonstration of in vitro hypoxia detection by Pt—POP under biological imaging conditions using an epi-fluorescence microscope. The progressive phosphorescence intensity signal increase immediately after oxygen levels are decreased below 20% for the Pt—POP aqueous solution in a Petri dish should be noted. Results for this sensor in conjunction with the excellent animal model for hypoxia, *C. elegans* worms, are shown in FIG. 17, whereas similar results in *E. coli* bacteria and in *D. rerio* zebra fish are shown in FIGS. 18 and 19, respectively. In FIG. 18, conditions were: 18A: *E. coli* bacteria with 64X, DIC; 18B: *E. coli* bacteria with 64X, 405-520,222 g, 0.4 ms; 18C: *E. coli* bacteria incubated with Pt—POP 64X, 405-520,222 g, 0.4 ms; 18D: *E. coli* bacteria incubated with Pt—POP on 8$^{th}$ day 64X, 405-520,222 g, 0.4 ms. In FIG. 19, pictures were taken for stationary fish directly after injection (A) and 7 minutes after induced hypoxia (B), and for a swimming fish (C).

Figure 20:
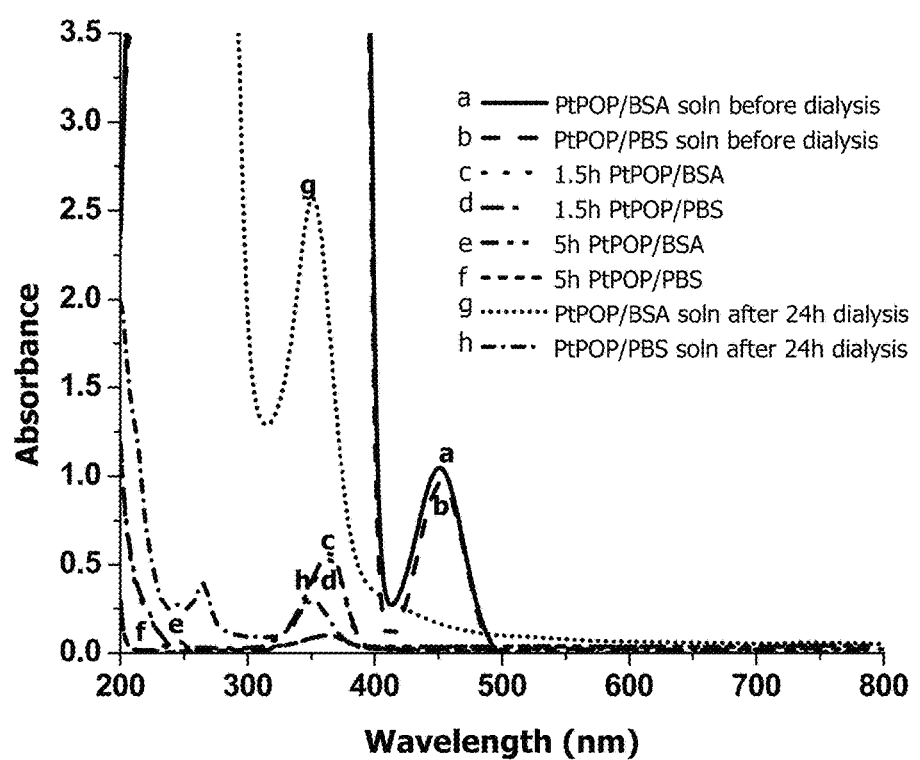
FIG. 20 shows absorbance versus wavelength for solutions of Pt—POP and PBS and Pt—POP labeled bovine serum albumin (BSA) under different conditions.

Though having a remarkably-high phosphorescence quantum yield (>70%) in deaerated (oxygen-free) aqueous solutions, Pt—POP suffers from long-term instability in solution. In presence of a biocompatible polymer such as chitosan or PAN, the stability of Pt—POP has been dramatically enhanced from minutes to years. This phosphorescent molecular system is also useful for labeling proteins. A common model protein (BSA=bovine serum albumin) was labeled with Pt—POP to enable BSA differentiation, with oxygen sensitivity, in biological media. See FIG. 20. FIG. 20 shows absorbance results demonstrating the ability of Pt—POP to be used as a biomolecule labelling agent. The results are demonstrated using highly common Bovine Serum Albumin (BSA) protein, and the data shows time dependent absorbance changes for BSA protein labelled with Pt—POP. After 24 hours of dialysis, the control (PBS) containing Pt—POP has approximately 10 times lower absorbance compared to BSA containing Pt—POP sample, which indicates that BSA has binding affinity to Pt—POP and Pt—POP can be used as a biomolecule labelling agent.

Example 10. NMR Data

Figure 21:
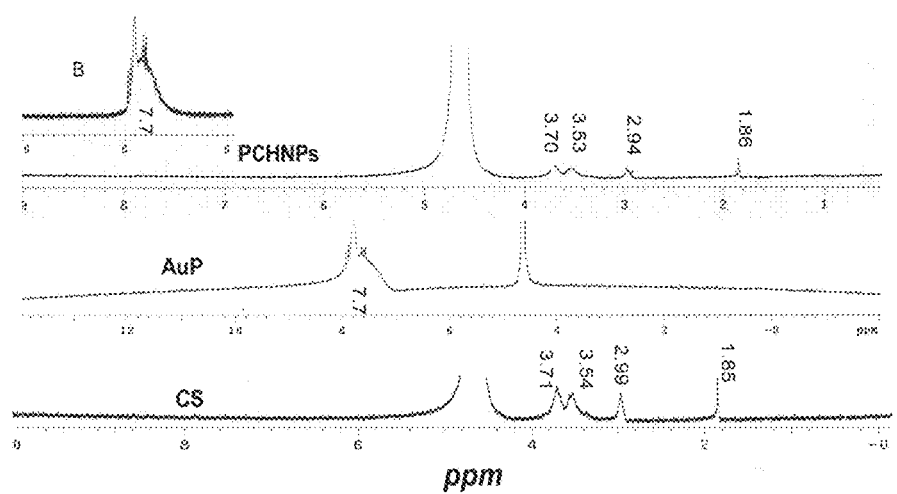
FIG. 21 shows $^1$H NMR data of Chitosan, AuP and PCHNPs acquired in $D_2O$ at ambient temperature.

FIG. 21 shows $^1$H NMR data of Chitosan, AuP and PCHNPs acquired in D$_2$O at ambient temperature. Data were acquired using a Varian nuclear magnetic resonance (NMR) spectrometer operating at 500 MHz.

What is claimed is:

1. Phosphorescent hydrogel nanoparticles, comprising:
polyanionic metal phosphors having light emitting properties, wherein the polyanionic metal phosphors are "PtP," wherein "PtP" is $Pt^{II}(ptp)_2$, and wherein ptp is 3,5-bis(pyridyl)-1,2,4-triazolate); and
biocompatible linear polymers, wherein the biocompatible linear polymers are cross-linked and complexed through electrostatic interactions with the polyanionic metal phosphors, and wherein the polyanionic metal phosphors emit light when complexed with the biocompatible linear polymers.

2. The phosphorescent hydrogel nanoparticles of claim 1, wherein the biocompatible linear polymers are chitosan polymers, poly-L-lysine (PLL), poly-ethyleneimine (PEI), poly-diallyldimethylammonium chloride (PDADMAC), polyacrylo nitrile (PAN), polyacrylic acid (PAA), or a combination thereof.

3. The phosphorescent hydrogel nanoparticles of claim 1, wherein the biocompatible linear polymers are chitosan polymers.

4. Phosphorescent hydrogel nanoparticles, comprising:
polyanionic metal phosphors having light emitting properties, wherein the polyanionic metal phosphors are "Pt-POP," wherein "Pt-POP" is $M_4[Pt_2(P_2O_5H_2)_4] \cdot 2H_2P$, and wherein $P_2O_5H_2$ is dihydrotetrakis(pyrophosphite) and M is potassium or sodium; and
biocompatible linear polymers, wherein the biocompatible linear polymers are cross-linked and complexed through electrostatic interactions with the polyanionic metal phosphors, and wherein the polyanionic metal phosphors emit light when complexed with the biocompatible linear polymers.

5. The phosphorescent hydrogel nanoparticles of claim 4, wherein the biocompatible linear polymers are chitosan polymers, poly-L-lysine (PLL), poly-ethyleneimine (PEI), poly-diallyldimethylammonium chloride (PDADMAC), polyacrylo nitrile (PAN), polyacrylic acid (PAA), or a combination thereof.

6. The phosphorescent hydrogel nanoparticles of claim 4, wherein the biocompatible linear polymers are chitosan polymers.

* * * * *

UNITED STATES PATENT AND TRADEMARK OFFICE
CERTIFICATE OF CORRECTION

PATENT NO. : 10,253,255 B2  
APPLICATION NO. : 15/365031  
DATED : April 9, 2019  
INVENTOR(S) : Mohammad A. Omary et al.

Page 1 of 1

It is certified that error appears in the above-identified patent and that said Letters Patent is hereby corrected as shown below:

In the Specification

1. In Column 5, Line 57, delete "dihydrotetrakis(pyrophosphito)" and insert -- dihydrotetrakis(pyrophosphite) --, therefor.
2. In Column 7, Line 61, delete "MQ-cm" and insert -- MΩ-cm --, therefor.
3. In Column 9, Line 2, delete "(25 L/well)." and insert -- (25 µL/well). --, therefor.
4. In Column 9, Lines 19-20, delete "thetrahydrothiophene" and insert -- tetrahydrothiophene --, therefor.
5. In Column 12, Line 14, delete "[Au(TPPTS)$_3$]$^{8"}$" and insert -- [AuTPPTS)$_3$]$^{8-}$ --, therefor.
6. In Column 14, Line 32, delete "M solutions," and insert -- µM solutions, --, therefor.
7. In Column 14, Line 64, delete "(L scale)" and insert -- (µL scale) --, therefor.

In the Claims

8. In Column 20, Line 5, in Claim 4, delete ".2H$_2$P," and insert -- .2H$_2$O, --, therefor.

Signed and Sealed this  
Tenth Day of September, 2019

Andrei Iancu  
*Director of the United States Patent and Trademark Office*